US009150571B2

(12) United States Patent
Hamill et al.

(10) Patent No.: US 9,150,571 B2
(45) Date of Patent: Oct. 6, 2015

(54) CRYSTALLINE FORMS OF FUSED AMINO PYRIDINES AS HSP90 INHIBITORS

(71) Applicant: Debiopharm International SA, Lausanne (CH)

(72) Inventors: Noel Hamill, Belfast (GB); James Moody, Portadown (GB); Sébastien Chabaud, Lausanne (CH); Arnaud Hamel, Bussigny-sur-Lausanne (CH)

(73) Assignee: Curis, Inc., Lexington, MA (US)

( * ) Notice: Subject to any disclaimer, the term of this patent is extended or adjusted under 35 U.S.C. 154(b) by 0 days.

(21) Appl. No.: 14/034,007

(22) Filed: Sep. 23, 2013

(65) Prior Publication Data

US 2014/0088138 A1   Mar. 27, 2014

Related U.S. Application Data

(63) Continuation of application No. PCT/IB2012/000608, filed on Mar. 26, 2012.

(30) Foreign Application Priority Data

Mar. 25, 2011   (WO) .................. PCT/IB2011/000644

(51) Int. Cl.
C07D 471/04 (2006.01)
A61K 31/437 (2006.01)
(52) U.S. Cl.
CPC ............ C07D 471/04 (2013.01); A61K 31/437 (2013.01)

(58) Field of Classification Search
USPC .......................................... 514/303; 546/118
See application file for complete search history.

(56) References Cited

U.S. PATENT DOCUMENTS

2010/0184801 A1* 7/2010 Cai et al. ....................... 514/303

FOREIGN PATENT DOCUMENTS

WO     2008/115719 A1     9/2008

OTHER PUBLICATIONS

Bao, Clinical Cancer Research, 2009, 15, 4046-4057.*
Bao, Molecular Cancer Therapeutics, 2009, 8, 3296-3306.*
Byrn, S. et al., "Pharmaceutical Solids: A Strategic Approach to Regulatory Considerations," Pharmaceutical Research, 12: 945-954 (1995).

* cited by examiner

*Primary Examiner* — John Mabry
*Assistant Examiner* — Daniel Carcanague
(74) *Attorney, Agent, or Firm* — Elmore Patent Law Group, P.C.; Roy P. Issac; Carolyn S. Elmore, Esq.

(57) ABSTRACT

This invention relates to the discovery of novel forms of Compound 1, including solvates, hydrates, and other crystalline forms. These novel forms of Compound 1 may impart advantages in pharmaceutical formulations incorporating them, including improved stability and bioavailability.

22 Claims, 17 Drawing Sheets

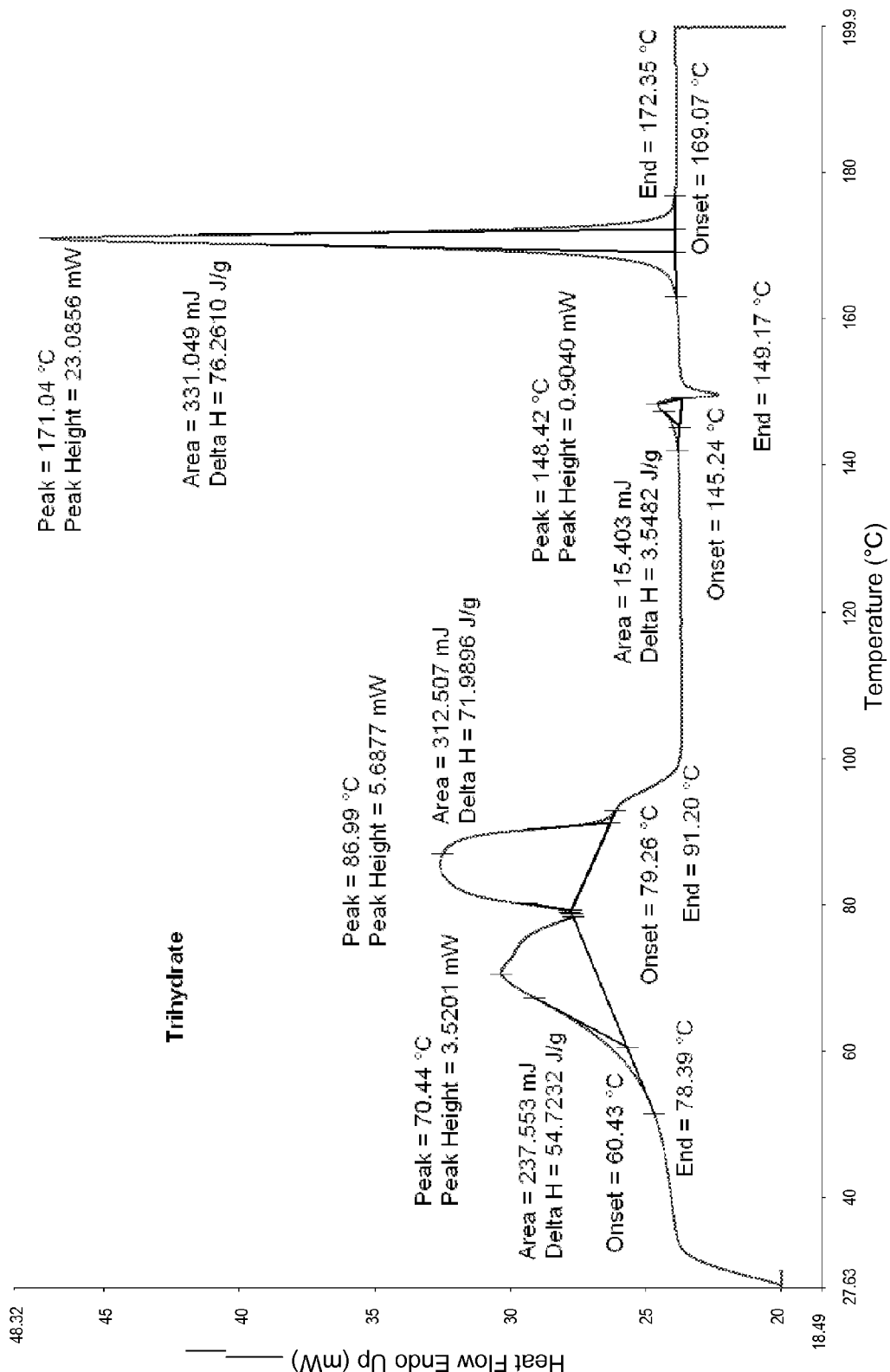

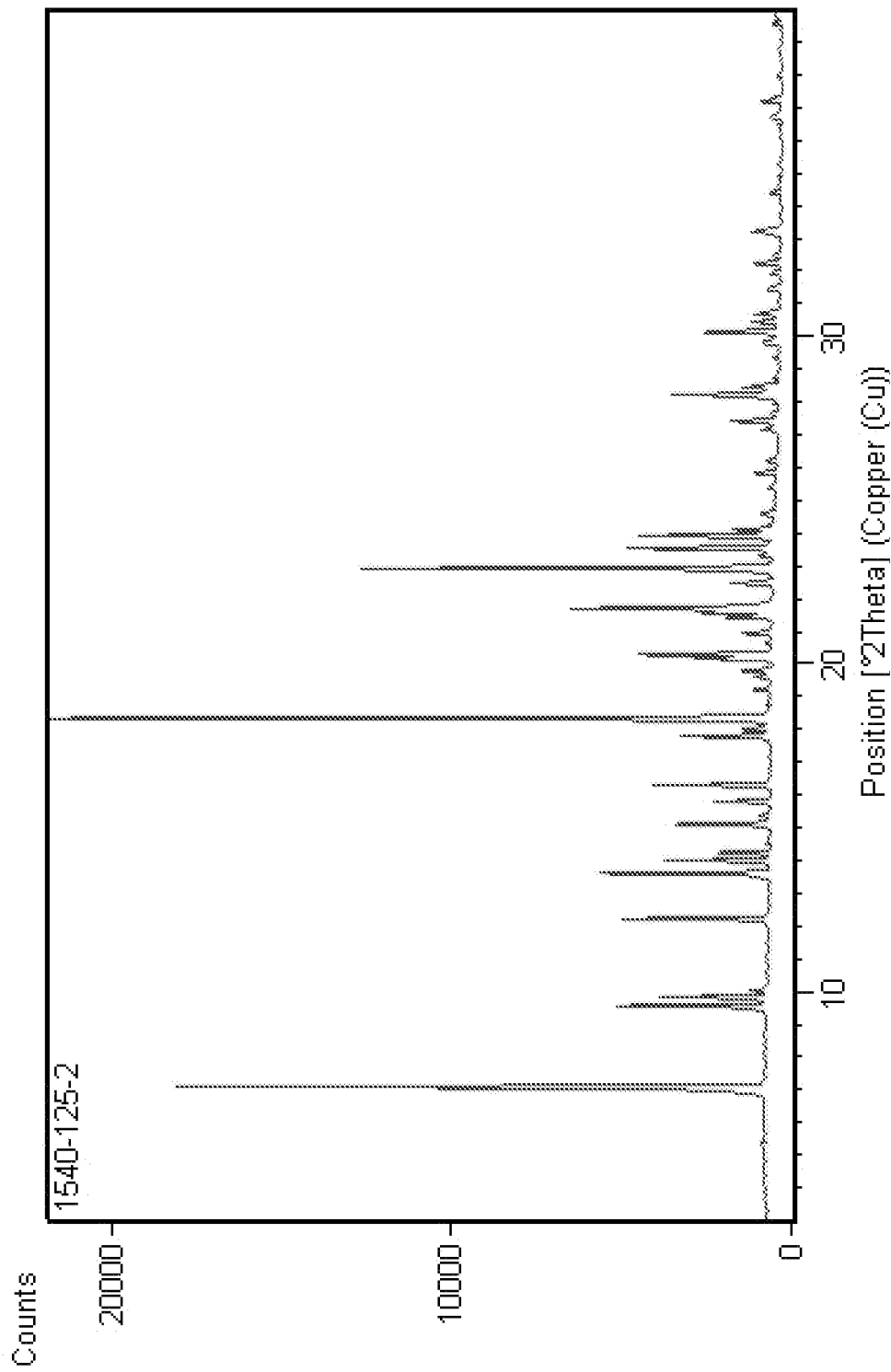

CRYSTALLINE FORMS OF FUSED AMINO PYRIDINES AS HSP90 INHIBITORS

RELATED APPLICATIONS

This application is a continuation of International Application No. PCT/IB2012/000608, which designated the United States and was filed on Mar. 26, 2012, published in English. The International Application No. PCT/IB2012/000608 claims the benefit of International Application No. PCT/IB2011/000644, which designated the United States and at least one other country and was filed on Mar. 25, 2011, published in English. The International Application No. PCT/IB2012/000608 claims benefit of International Application No. PCT/IB2011/000644 under 35 U.S.C 119(a)-(d) and 35 U.S.C 365(a). The entire teachings of the above applications are incorporated herein by reference.

HSP90s are ubiquitous chaperone proteins that are involved in proper protein folding and stabilization of a wide range of proteins, including key proteins involved in signal transduction, cell cycle control and transcriptional regulation. Researchers have reported that HSP90 chaperone proteins are associated with important signalling proteins, such as steroid hormone receptors and protein kinases, including, e.g.. Raf-1, EGFR, v-Src family kinases, Cdk4, and ErbB-2, many of which are overexpressed or mutated in various cancers (Buchner J. *TIBS,* 1999, 24, 136 141; Stepanova, L. et al. *Genes Dev.* 1996, 10, 1491 502; Dai, K. et al. *J. Biol. Chem.* 1996, 271, 22030-4). Studies further indicate that certain co-chaperones, e.g., HSP70, p60/Hop/Sti1, Hip, Bag1, HSP40/Hdj2/Hsj1, immunophilins, p23, and p50, may assist HSP90 in its function (Caplan, A. *Trends in Cell Biol.* 1999, 9, 262 68).

HSP90 has been shown by mutational analysts to be necessary for the survival of normal eukaryotic cells. However, HSP90 is over expressed in many tumor types indicating that it may play a significant role in the survival of cancer cells and that cancer cells may be more sensitive to inhibition of HSP90 than normal cells. For example, cancer cells typically have a large number of mutated and overexpressed oncoproteins that are dependent on HSP90 for folding. In addition, because the environment of a tumor is typically hostile due to hypoxia, nutrient deprivation, acidosis, etc. tumor cells may be especially dependent on HSP90 for survival. Moreover, inhibition of HSP90 causes simultaneous inhibition of a number of client oncoproteins, as well as hormone receptors and transcription factors making it an attractive target for an anti-cancer agent. In fact, benzoquinone ansamycins, a family of natural products that inhibit HSP90, has shown evidence of therapeutic activity in clinical trials. Several promising ansa-mycin related HSP90 inhibitors are currently in clinical trial namely, 17-allylamino 17-demethoxygeldanamycin (17-AAG), 17-dimethylaminoethylamino-17-demethoxygeldanamycin (17-DMAG) and IPI-504. Another class of the HSP90 inhibitor is the synthetic small molecule purine-scaffold. Currently, many of the purine-scaffold HSP90 inhibitors are showing positive preclinical results, with the front runner being CNF-2024, which is currently in phase 1 clinical trial.

Recent studies suggest that heat shock proteins (HSPs) play an important role in neurodegenerative disorders such as Parkinson's disease (PD), Alzheimer's disease (AD), amyotropic lateral sclerosis (ALS), Huntington disease (HD) (Luo, G-R. *Int. J. Biol. Sci.,* 2007, 3(1), 20-26; Dickey, C., *J. Clin. Invest.,* 2007, 117(3), p. 648-658). It has been shown that manipulation of HSPs, such as down regulation of HSP90 or up regulation of HSP70, affords beneficial effects in several neurodegenerative disorders either by reducing protein aggregation or facilitating proper folding of proteins to restore their function.

Drugs targeting the protein HSP90 are quite new in cancer and neurodegenerative disease therapies. A number of such promising drug candidates, including Compound 1 as depicted below, have been described by Cai et al. in WO 2008/115719 (Curis Inc.). In addition, polymorphs, solvates and salts of various drugs have been described in the literature as important in drug delivery to optimize properties such as solubility, stability and processing characteristics. The finding of polymorphic forms of HSP90 inhibitors, such as Compound 1 depicted below, thus presents additional opportunities in the treatment of cancer and neurodegenerative disorders.

SUMMARY OF THE INVENTION

The present invention relates to the discovery of novel crystalline forms of Compound 1:

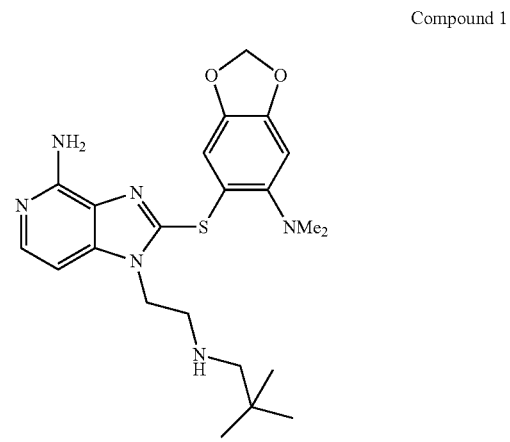 [SMILES: CN(C)c1cc2c(cc1Sc1nc3c(N)nccc3n1CCNCC(C)(C)C)OCO2]

Compound 1

Compound 1 is shown to have three anhydrous crystalline forms (Forms I, II and III), and two solvate forms a trihydrate and a toluene solvate. These novel forms can impart advantages in pharmaceutical formulations incorporating them, including improved shelf life and bioavailability.

The present invention provides crystalline forms of Compound 1 which are characterized by X-ray Powder Diffraction (XRPD), differential scanning calorimetry (DSC), hyper differential scanning calorimetry (hyper DSC), thermogravimetric/differential temperature analyst (TG/DTA), particle size distribution analysis, dynamic vapour sorption (DVS), and HPLC.

A further aspect of the invention provider pharmaceutical compositions containing the crystalline forms of Compound 1 disclosed herein and their use in the treatment of cancer and neurodegenerative diseases.

BRIEF DESCRIPTION OF THE DRAWINGS

The invention is illustrated, but in no way limited, by the Tables herein and the following examples, with reference to the figures in which.

DETAILED DESCRIPTION OF THE INVENTION

Figure 1A:
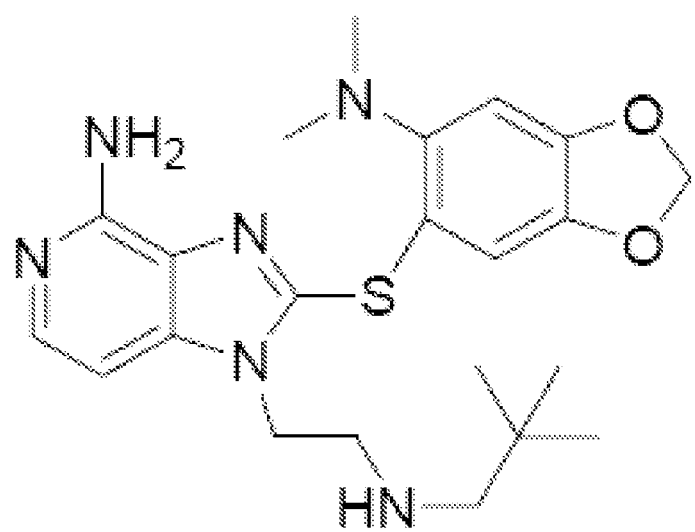
FIG. 1a depicts the chemical structure of Compound 1.
Figure 1B:
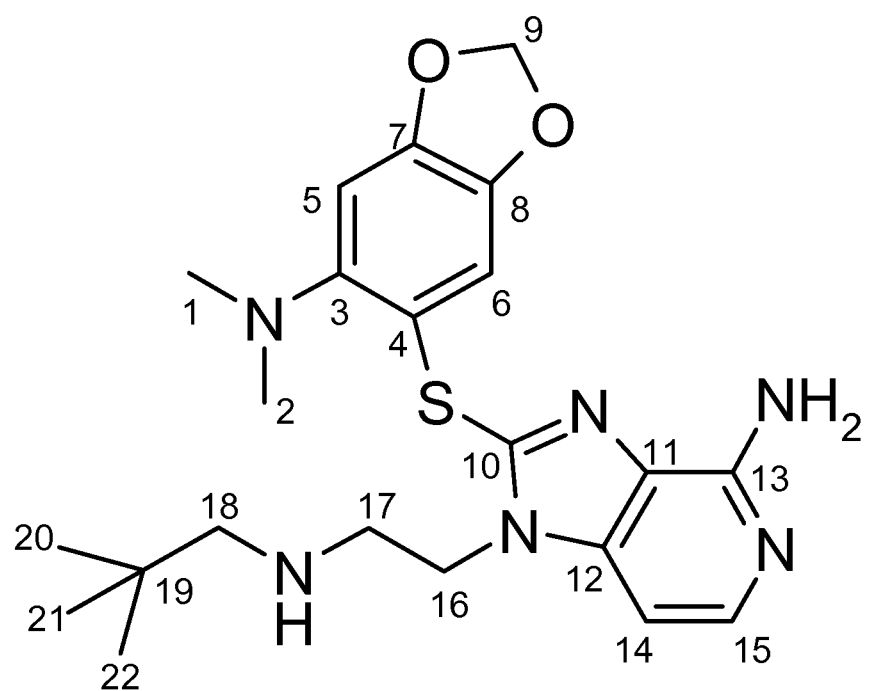
FIG. 1b depicts the atom numbering of Compound 1 for NMR assignment.

In the course of research, the inventors discovered several crystal forms of Compound 1. It was discovered that Compound 1 has three polymorphs (Forms I, II and III), a trihydrate and a toluene solvate. Form I was found to be the most thermodynamically stable polymorph at temperatures above about 18±2° C. but Form II was found to be the most thermodynamically stable polymorph below this temperature. The Inventors appreciate that the crystalline forms of Compound 1 may have good to superior properties in comparison with amorphous forms of Compound 1.

Although Form I is thermodynamically the most stable form above 18±2° C., it is unexpectedly difficult to prepare unless seeding is used or conditions are carefully controlled. Indeed, the GMP batch runs were observed to be mainly Form II. The surprising implication is that routine polymorph screening would have missed this form, with it only appearing at a later phase of development or after commercialisation.

Form II can be prepared even at high water activity, which is an unexpected property. The trihydrate is not prepared even near water activity near 0.4 where one would expect hydrates would form, should they exist. This is advantageous since water is ubiquitous during manufacture, processing and storage.

The trihydrate form has an intrinsic dissolution rate which is higher than anhydrous Forms I and II. It is well known, according to the Noyes-Whitney relationship, that hydrates have the lowest solubility in aqueous systems. Therefore, it is surprising that the trihydrate form of Compound 1 would show a faster dissolution rate compared to anhydrous Forms. The high water activity (~0.4) required to prepare the trihydrate is also unexpected.

Form III has the advantage of being the most soluble Form, with a higher dissolution rate than Form I, II and trihydrate. This is surprising given the structural similarity between Form III and Form II, as evidenced by their similar XRPD patterns.

Pharmaceutical compositions of Compound 1 when formulated for administration are useful in the treatment of, for example, cancer and neurodegenerative disorders, as well in the treatment of other disorders that relate to HSP90 inhibition.

As with all pharmaceutical compounds and compositions, the chemical and physical properties of the HSP90 inhibitor form(s) utilized can be important in its commercial development. These properties include, but are not limited to: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture, and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, processing and storage of pharmaceutical compositions comprising Compound 1. Solid state forms of HSP90 inhibitors that provide an improvement in one or more of these properties relative to other solid state forms of HSP90 inhibitors are desirable.

The polymorphs of the invention and the compositions containing them have the advantage that they are in a form which provides for improved ease of handling. Further, depending upon the intended use, they have improved chemical and solid state stability. For example, they may be stable when stored over prolonged periods of time. They may be prepared in good yields, in higher purity, in less time, more conveniently and at a lower cost, than forms prepared previously. They may also provide improved bioavailability.

Of particular interest to those skilled in the art is a crystalline form of the inversion wherein the form is substantially pure. Other polymorphs, including the solvates specifically described herein and combinations thereof, are a part of the invention.

1. Interconversion Experiments

Interconversion experiments were carried out using Forms I, II and III at 5° C., 10° C., 15° C., 21° C. and 60° C. in ethyl acetate. Suspensions of approximately equivalent amounts (about 75 mg) of each form in ethyl acetate (1.2 mL) were prepared and agitated at different temperatures. The slurries were stirred and sampled periodically (200 μL aliquot) after 30 mins and over the period of 10 days or until when near complete or complete conversion had occurred. The sampled aliquot was filtered, air dried and analyzed by XRPD.

2. Instrumental Techniques

XRPD

X-Ray Powder Diffraction (XRPD) analyses were performed using a Panalytical Xpert Pro diffractometer equipped with a Cu X-Ray tube and a Pixcel detector system. The samples were analyzed in transmission mode and held between low density polyethylene films. XRPD patterns were sorted and manipulated using HighScore Plus 2.2 software.

DSC

Differential Scanning Calorimetry (DSC) analyses were carried out on a Perkin Elmer Jade Differential Scanning Calorimeter. Accurately weighed samples were placed in crimped aluminium pans. Each sample was held isothermally at 30° C. for 1 minute and heated from 30° C. to 300° C., under $N_2$, at a rate of 10° C./min. Temperatures were reported at the transition onset, to the nearest 0.01° C.

Hyper DSC

Hyper Differential Scanning Calorimetry (hyper DSC) analyses were carried out on a Perkin Elmer Diamond Differential Scanning Calorimeter. Accurately weighed samples were placed in crimped aluminium pans. Each sample was heated and cooled under helium at a rate of 300° C./minute using a temperature range of −50 to 210° C. Indium metal was used as the calibration standard.

Hyper DSC allows the measurement of thermal events using very fast scanning rates. The fast scanning rate results in a much increased heat flow signal and therefore greatly increases sensitivity. This allows extremely low energy transitions, such as the glass transition temperature ($T_g$), to be identified and measured much more effectively.

TG/DTA

Thermogravimetric (TG) analyses were carried out on a Perkin Elmer Diamond Thermogravimetric/Differential Temperature Analyser (TG/DTA). The calibration standards were Indium and Tin. Samples were placed in an aluminium sample pan, inserted into the TG furnace and accurately weighed. The samples were held isothermally at 30° C. for 1 minute and heated from 30° C. to 300° C. in a stream of $N_2$ at a rate of 10° C./min. The temperature of the furnace was equilibrated at 30° C. prior to the analysis of the samples.

Particle Size Distribution Analysis

Sympatec HELOS Laser Diffraction was used to determine the particle size distribution of the Compound 1 sample using a dry powder dispersion method. The method parameters used to analyse Compound 1 Form I are given as follows:

Lens: R4 (Range 1.8-350 μm)
Primary Nitrogen Flow: 3.5 bar
Trigger Conditions: Channel 28>0.5<0.2
Feed Rate (VIBRI): 85% VIBRI
Feed Gap: 1.5 mm
Reference Time: 15 seconds
Analysis: HRLD Dynamic Vapour Sorption (DVS)

Dynamic Vapour Sorption (DVS) was performed using a Hiden Analytical Instruments IGAsorp Vapour Sorption Balance. Approximately 15 mg of sample was placed into a wire-mesh vapour sorption balance pan, loaded into the IGAsorp vapour sorption balance and held at 25° C.±0.1° C. The sample was subjected to a step profile from 0 to 90% RH at 10% increments, followed by desorption from 85% RH to 0% RH at 10% increments. The equilibrium criterion was set to 99.5% step completion within a minimum of 60 minutes and a maximum of 10 hours for each increment. The weight change during the sorption cycle was monitored, allowing for the hygroscopic nature of the sample to be determined. The data collection interval was in seconds.

HPLC

The HPLC method used to determine purity (area %) is outlined in Table 1. The retention time of Compound 1 was typically 10.0±0.2 min and no new peaks were detected during the analysis of experimental samples.

TABLE 1

HPLC Operating Method tor Purity Analysis of Compound 1 Samples

| PARAMETER | CONDITIONS | |
|---|---|---|
| HPLC System | Agilent | |
| Column | Phenomenex Luna phenyl-hexyl, 5 μm, 4.6 × 250 mm | |
| Oven Temperature | 25° C. | |
| Flow Rate | 1.5 mL/min | |
| Injection Volume | 15 μL | |
| Mobile Phase | Mobile Phase A: 0.05% TFA in water Mobile Phase B: Acetonitrile | |
| Run Time | 31 minutes | |
| Post Run | 9 minutes | |
| Gradient | Time | Mobile Phase A | Mobile Phase B |
| | 0 | 100 | 0 |
| | 1 | 100 | 0 |
| | 18 | 50 | 50 |
| | 28 | 10 | 90 |
| | 30 | 10 | 90 |
| | 31 | 100 | 0 |

For intrinsic dissolution studies (IDR) an isocratic HPLC method with a shorter run time (10 mins) was used due to the high number of sample analyses required (Table 2).

TABLE 2

HPLC Operating Method for IDR and Equilibrium Solubility Analysis of Compound 1 Samples

| PARAMETER | CONDITIONS |
|---|---|
| HPLC System | Agilent |
| Column | Phenomenex Luna phenyl-hexyl, 5 μm, 4.6 × 250 mm |
| Oven Temperature | 25° C. |
| Flow Rate | 1.5 mL/min |
| Injection Volume | 15 μL |
| Mobile Phase | Mobile Phase A: 0.05% TFA in water:Acetonitrile (80:20 v/v) |
| 1. Run Time | 10 minutes |

Specific Surface Area

A weighed quantity of each sample (about 0.5 g) was introduced to the sample tubes and degassed for 24 hours under nitrogen at room temperature. The samples were reweighed and assessed for BET surface area between 0.06 and 0.2 relative pressure (P/Po) using a Micromeritics Tristar 3000. The gases used for the analysis were nitrogen and helium.

3. Bulk Density Method

Measurement in a Graduated Cylinder

A sufficient amount of material was passed through a 1.0 mm sieve in order to dispense agglomerates that may have formed during storage. The material was carefully placed into either a pre-tared 10 mL or 25 mL graduated cylinder which was readable to 0.2 mL to avoid compacting. The weight and the unsettled apparent volume ($V_o$) of the material were recorded. $V_o$ was recorded to the nearest graduated unit. The bulk density value was calculated using Equation 1.

$$\text{Bulk Density} = \frac{\text{Mass of Material (grams)}}{\text{Volume of material (mL)}} \quad \text{Equation 1}$$

4. Solubility Determinations

EP Method

Sample Preparation

All samples to be tested were passed through number 180 and number 125 sieves to ensure that they were finely powdered prior to testing, i.e. not less than 95% of sample mass passed through a 4 μm sieve and not more than 40% passed through a 38 μm sieve.

Dissolving Procedure

The vial containing the test material and chosen solvent was shaken on a vortex mixer for 1 minute. The vial was placed in a water bath maintained at 25° C.±0.5° C. for 15 minutes. If particles were still remaining, the vial was shaken again for 1 minute using the vortex mixer and returned to the water bath for a further 15 minutes.

Procedure

Approximately 100 mg of the test material was weighed into a vial and 0.1 mL of the chosen solvent was added. This was treated as described in the procedure above. If the material did not totally dissolve, a further 0.9 mL of solvent was added to the vial and treated as described in the dissolving procedure. If the material still failed to dissolve, further aliquots of solvent were added i.e. 2.0 mL and 7.0 mL. After each addition of solvent the contents of the vial were treated as described in the dissolving procedure. If after the addition of the last aliquot of solvent (7.0 mL) the material still did not dissolve, approximately 10 mg of material was weighed into a fresh vial and 10.0 mL of solvent added and treated as described in the dissolving procedure. After the dissolving procedure was complete, the solubility of the material was visually determined. If material did not completely dissolve, approximately 1 mg of material was weighed into a new vial and 10.0 mL of solvent added and again treated as outlined in the dissolving procedure. Results obtained were reported.

Equilibrium Method

Approximately 25 mg of test substance was weighed into glass test tubes. The relevant volume of buffer solution (10 mL) was added to each vessel. The tests were performed in duplicate. The vessels were lightly sealed and agitated at 25°C. in a shaking thermostatted water bath protected from light. Sampling was performed after 24 hours and thereafter not less than 20 hours between sample time points. Sampling was performed by filtration of a portion of the test slurry through a 0.2 μm filter and dilution in appropriate media for HPLC analysis.

If the concentrations measured at the two time points did not differ by more than 15%, the test was regarded as satisfactory. If the results showed a tendency of increasing values, a later time point was taken.

Equilibrium solubility was determined by HPLC by using:

$$\text{Concentration Standard(mg/g)} = \frac{\text{Peak Area of Sample}}{\text{Peak Area of Standard}} \times \text{Standard Concentration} \times \text{Purity(mg/g)}$$

where the Standard Purity was taken as 95%.

Buffer pH 7.0 samples were prepared by removing approximately 1 mL of the solution from the appropriate glass test tube and filtering into a HPLC vial using a PTFE 0.2 μm syringe filter. The concentration of the Compound 1 in the filtrate was determined by comparison with data of the standard sample (about 0.25 mg/g).

Buffer pH 5.0 samples were prepared by removing approximately 1 mL of the solution from the appropriate glass test tube and filtering into a HPLC vial using a PTFE 0.2 μm syringe filter. The filtered solution was diluted by a factor of 5 and approximately 1 mL of this solution was added into a HPLC vial for analysis. The concentration of the Compound 1 in the filtrate was determined by comparison with data of the standard sample (about 0.25 mg/g).

At the end of the solubility study, the solids were isolated from the experimental slurries, filtered, dried and analyzed by XRPD in order to determine the physical form.

5. Intrinsic Dissolution Rate (IDR)

Distek 8 mm intrinsic dissolution apparatus was used for the study. The three fixed screws on the surface plate were inserted through the three holes on the die and fastened with the supplied washers and nuts. 100 mg of test material was placed in the die cavity. The punch was inserted into the cavity and compressed, with the aid of a bench top hydraulic press for 30 sec at 1 ton pressure. The surface plate was disconnected from the die to expose a compact pellet of 0.5 cm$^2$ surface area. The pellets were checked for any breaks and cracks on the surface. Only the pellets with flat even surface with no irregularities were used for the study. The Viton gasket was placed around the threaded shoulder of the die and a polypropylene cap was screwed on to the threads. The assembly was immersed, pellet side up, into the bottom of the dissolution vessel (flat bottom) containing dissolution medium at 37° C. The media is degassed under helium purge for 15 min prior to use.

Dissolution Conditions
Dissolution media: pH 5.0 USP buffer
Vessel volume: 900 mL
Rotation speed: 50 RPM
Temperature: 37° C.±0.5° C.
Sampling time points: 30, 60, 90, 120 and 150 mins
Sample size: 1 mL
Sample analysis: By HPLC (conditions in Table 2 above)

The present invention provides a method for the treatment of a patient afflicted with cancer or central nervous system disorders wherein such disease states may be treated by the administration of an effective amount of Compound 1 of the present invention to a patient in need thereof.

Thus, where the composition is being administered to treat cancer or a central nervous system disorder, a therapeutically effective amount of Compound 1 is, preferably, an amount effective in controlling or reducing the disease or disorder. The term "controlling" is intended to refer to all processes wherein there may be a slowing, interrupting, arresting, or stopping of the disease or disorder, or other characteristic of the disease or disorder, and does not necessarily indicate a total elimination of all disease or disorder symptoms.

The term "therapeutically effective amount" is further meant to define an amount resulting in the improvement of any parameters or clinical symptoms. The actual dose may vary with each patient.

As used herein, the term "subject" or "patient" refers to a warm blooded animal, including but not limited to humans, such as a mammal which is afflicted with a particular disease state.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal, its size, age, and general health; the specific disease involved; the degree of or involvement or the seventy of the disease; the response of the individual patient; the particular compound administered; the mode of administration; the bioavailability characteristic of the preparation administered; the dose regimen selected; the use of concomitant medication; and other relevant circumstances.

Preferred amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described for example in Remington's Pharmaceutical Sciences, latest edition, Mack Publishing Co.

Pharmaceutical compositions can be manufactured utilizing techniques Known in the art. Typically, the therapeutically effective amount of the compound will be admixed with a pharmaceutically acceptable carrier.

The compounds or compositions of the present invention may be administered by a variety of routes, for example, by enteral, oral, buccal, rectal, vaginal, dermal, nasal, bronchial, tracheal, pulmonary, parenteral, subcutaneous, intravenous, intramuscular, or intraperitoneal route, by injection, ingestion, or inhalation, for example.

For oral administration, the compounds can be formulated, for example, in a solid such as capsules, pills, tablets, lozenges, melts, powders, or in a form for mixing into a solution, suspension or emulsion.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. It is worth noting that the trihydrate form of compound 1 appears to be particularly appropriate for the manufacture of tablets.

Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension, illustrative of suitable pharmaceutical carriers include wafer, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably, topical administration will be accomplished using a patch either of the reservoir and porous membrane type or of a solid matrix variety.

For surgical implantation, the active ingredients may be combined with any of the well-known biodegradable and bioerodible carriers, such as polylactides and poly-lactide-co-glycolids and collagen formulations. Such materials may be in the form of solid implants sponges, and the like. In any event, for local use of the materials, the active ingredients usually be present in the carrier or excipient in a weight ratio of from about 1:1000 to 1:20,000, but are not limited to ratios within this range.

When the composition is to be used as an injectable material, including but not limited to needle-less injection, it can be formulated into a conventional injectable carrier. Suitable carriers include biocompatible and pharmaceutically acceptable solutions.

EXAMPLE

Example 1

Preparation of Forms I, II, III and Trihydrate of Compound 1

Example 1.1.1

Preparation of Form I of Compound 1 (Small Scale; Best Practice Mode)

Ethyl acetate (9 g, 10 mL) was added to Compound 1 (Form II or III or mixtures thereof, 3.0 g) and heated to 60° C. to form a suspension. This was stirred at 60° C. for 30 minutes and cooled to 20° C. at 0.2° C./min, stirred at 20° C. for 120 minutes and isolated by filtration. The solid was dried under vacuum at 40-50° C. with a slight nitrogen bleed to yield 2.4 g (60%). XRPD confirmed the solid to be pure Form I. The Compound 1 used in this final step was obtained from evaporation from ethyl acetate solution. A lab experiment repeating evaporation of ethyl acetate solution yielded Form III (see example 2.4 below).

The initial temperature (60° C.), final temperature (20° C.) and cooling rate are all critical parameters for the isolation of pure Form I. Suspension at lower temperature did not yield Form I (see example 2.2), isolation at temperatures lower than 20° C. risks inter-conversion to other Forms (see example 4) and faster cooling rate risks nucleation of the other Forms (see example 2.5.1).

Example 1.1.2

Preparation of Form I of Compound 1 (Larger Scale)

Compound 1 (441.84 g) and ethyl acetate (1015 mL) were added to a 2L flask fitted with mechanical stirrer and thermometer and heated using an oil bath to about 60° C. When internal temperature of the mixture reached about 56° C., the suspension was seeded with Form I crystals obtained using the small scale experiment (about 20 mg). After continued stirring for 18 hrs, the mixture was sampled for XRPD analysis, which indicated full conversion to Form I. The slurry was filtered through a sinter funnel under vacuum. Mother liquor was used to wash remaining solid out of flask. The solid was left to dry on the filter under vacuum for about 2 hours, transferred to a large Petri dish and further dried under vacuum overnight. The amount recovered was 412.35 g (93.3%).

Example 1.2

Preparation of Form II of Compound 1

Figure 2:
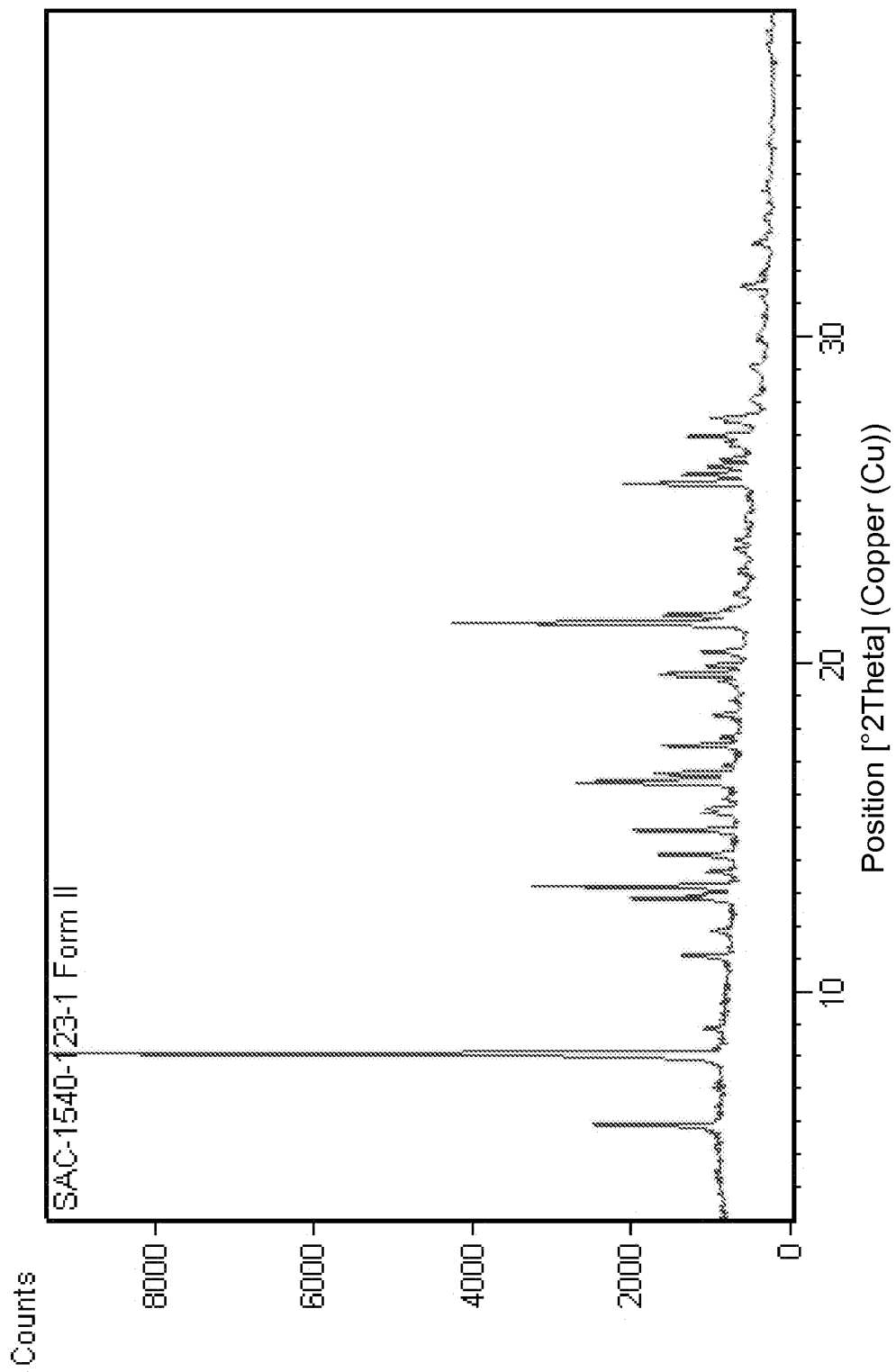
FIG. 2a-c is a graph depicting the (a) XRPD (b) DSC and (c) TG/DTA analysis of Compound 1 Form II.
Figure 2:
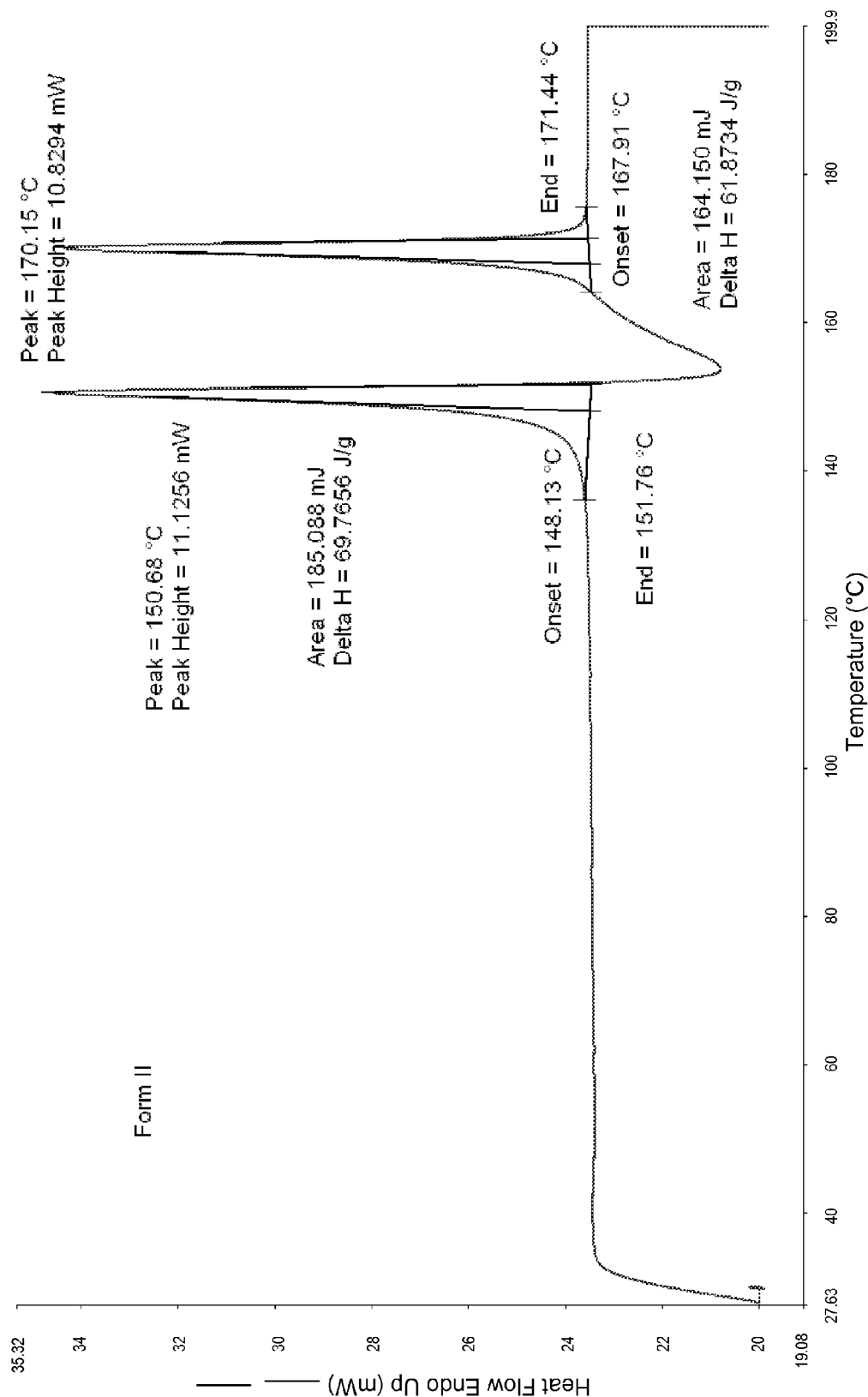
Figure 2:
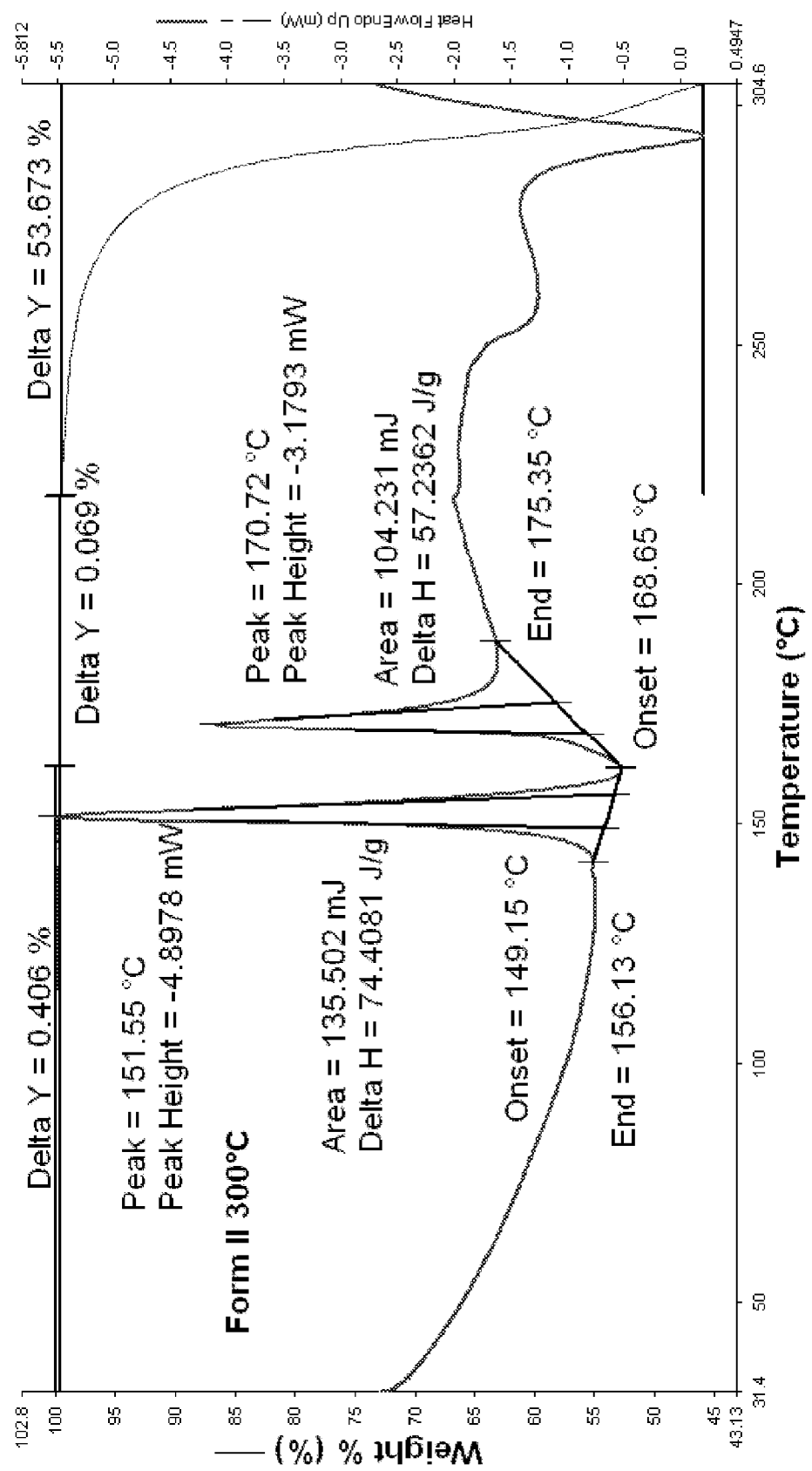

Compound 1 (1.59 g) was weighed into a vial and THF (2.25 mL) added. The resultant slurry was shaken for 5 days at ambient temperature. The solid was recovered by filtering the slurry under vacuum. After the solid had been dried on the filter for about 2 hours, (61.4% recovery) the sample was analyzed by XRPD, DSC and TGA (FIG. 2).

Example 1.3.1

Preparation of Form III of Compound 1 (Small Scale)

Compound 1 was weighed out and butan-1-ol (400 μL) added. The mixture was heated to 60° C. for 45 minutes to result in a warm suspension. The warm suspension was filtered through a heated (50° C.) 0.2 μm syringe filter into a heated (40° C.) HPLC vial. The filtered solution was then cooled immediately to −35° C. in a dry ice/acetonitrile bath.

Example 1.3.2

Preparation of Form III of Compound 1 (Larger Scale)

Figure 3:
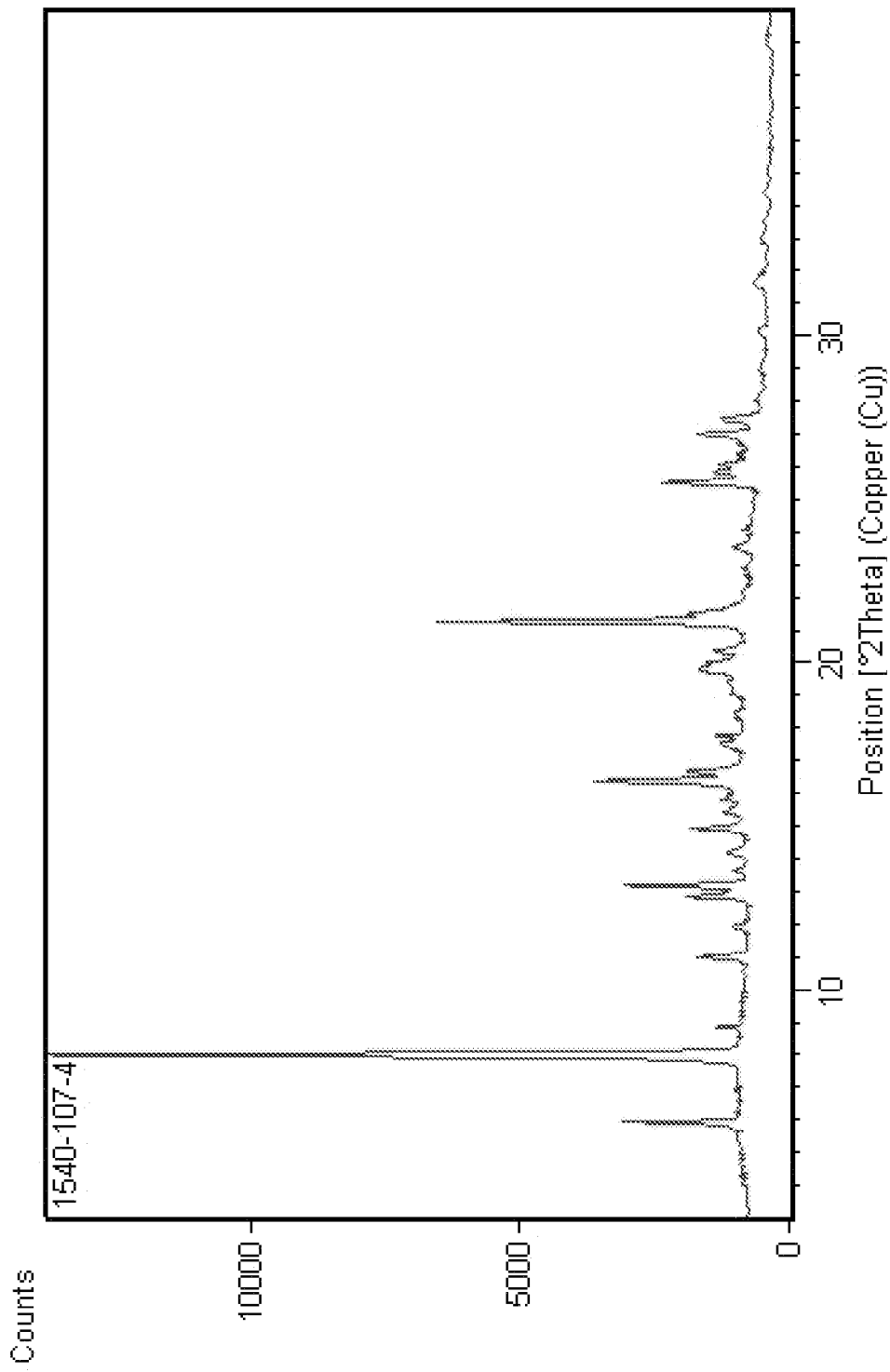
FIG. 3a-c is a graph depicting the (a) XRPD, (b) DSC and (c) TG/DTA analysis of Compound 1 Form III.
Figure 3:
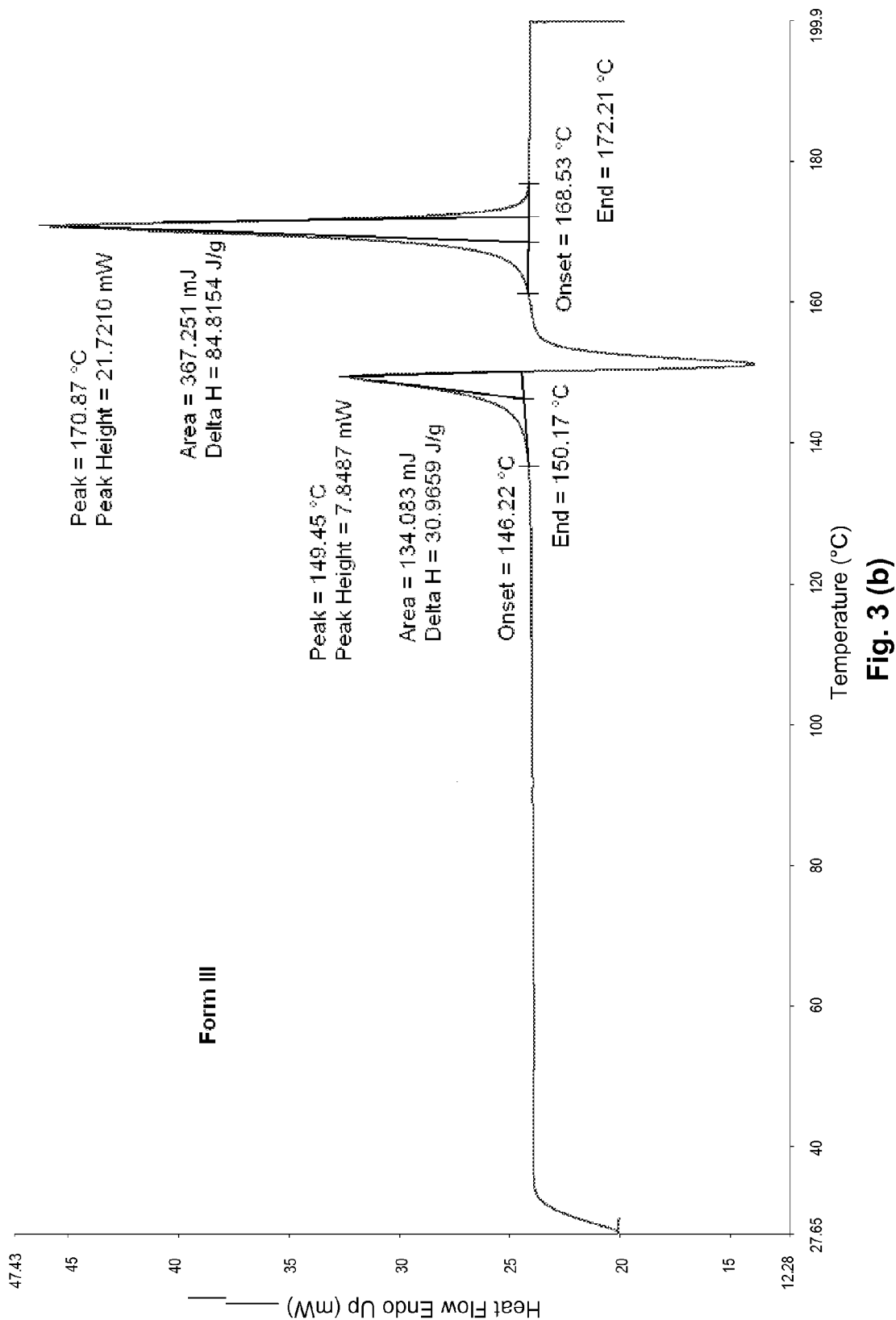
Figure 3:
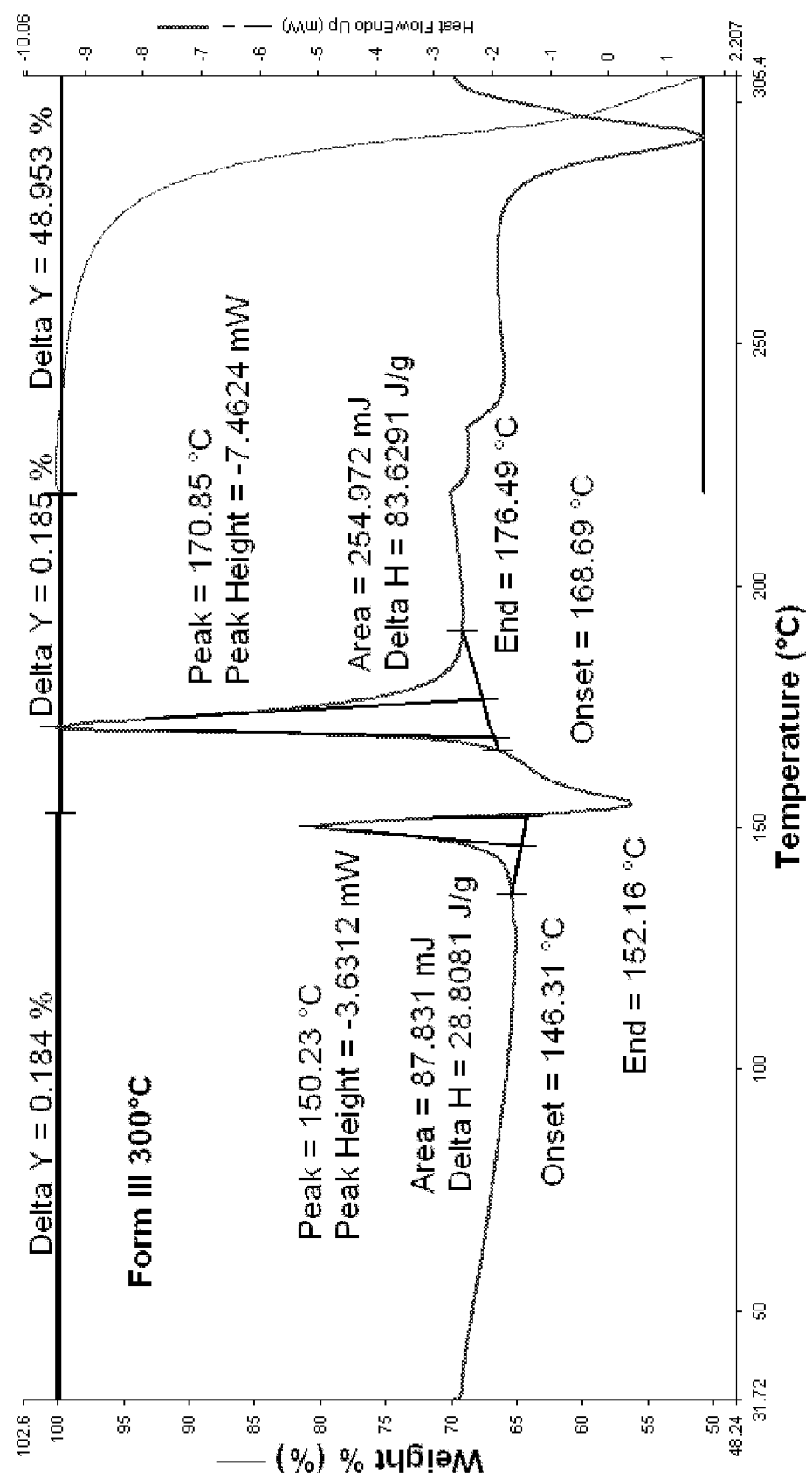

Compound 1 was weighed out (2.4 g) and butan-1-ol (8.8 mL) added. The mixture was heated with stirring in an oil-bath at 60° C. for 30 minutes. The warm suspension was filtered through a heated (about 50° C.) 0.45 μm syringe filter into a heated (about 50° C.) vial. Form III seeds from the small scale experiment were added and the mixture was cooled immediately to −35° C. in a dry ice/acetonitrile bath and left at this temperature for 45 minutes. It was placed in a refrigerator (<5° C.) for 2 hours and filtered under vacuum. The solid was dried on the filter under vacuum for approximately 2 hours, and then dried in vacuum oven at ambient temperature overnight (45% yield). The solid generated was analyzed by XRPD, DSC and TGA (FIG. 3). HPLC analysis indicated 99.6% purity (area).

Example 1.4

Preparation of Trihydrate of Compound 1

Figure 4:
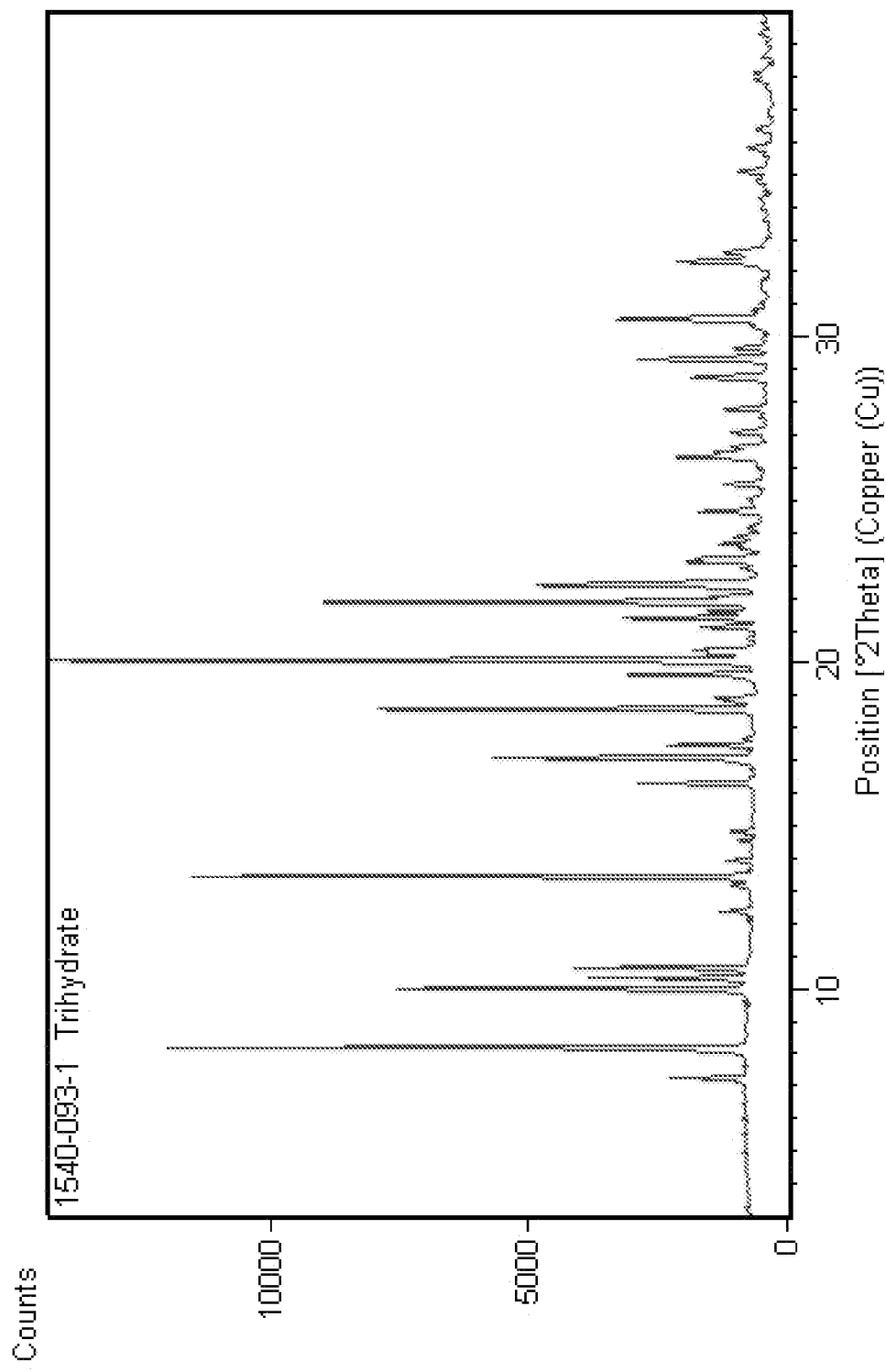
FIG. 4a-c is a graph depicting the (a) XRPD, (b) DSC and (c) TG/DTA analysis of Compound 1 trihydrate.
Figure 4:
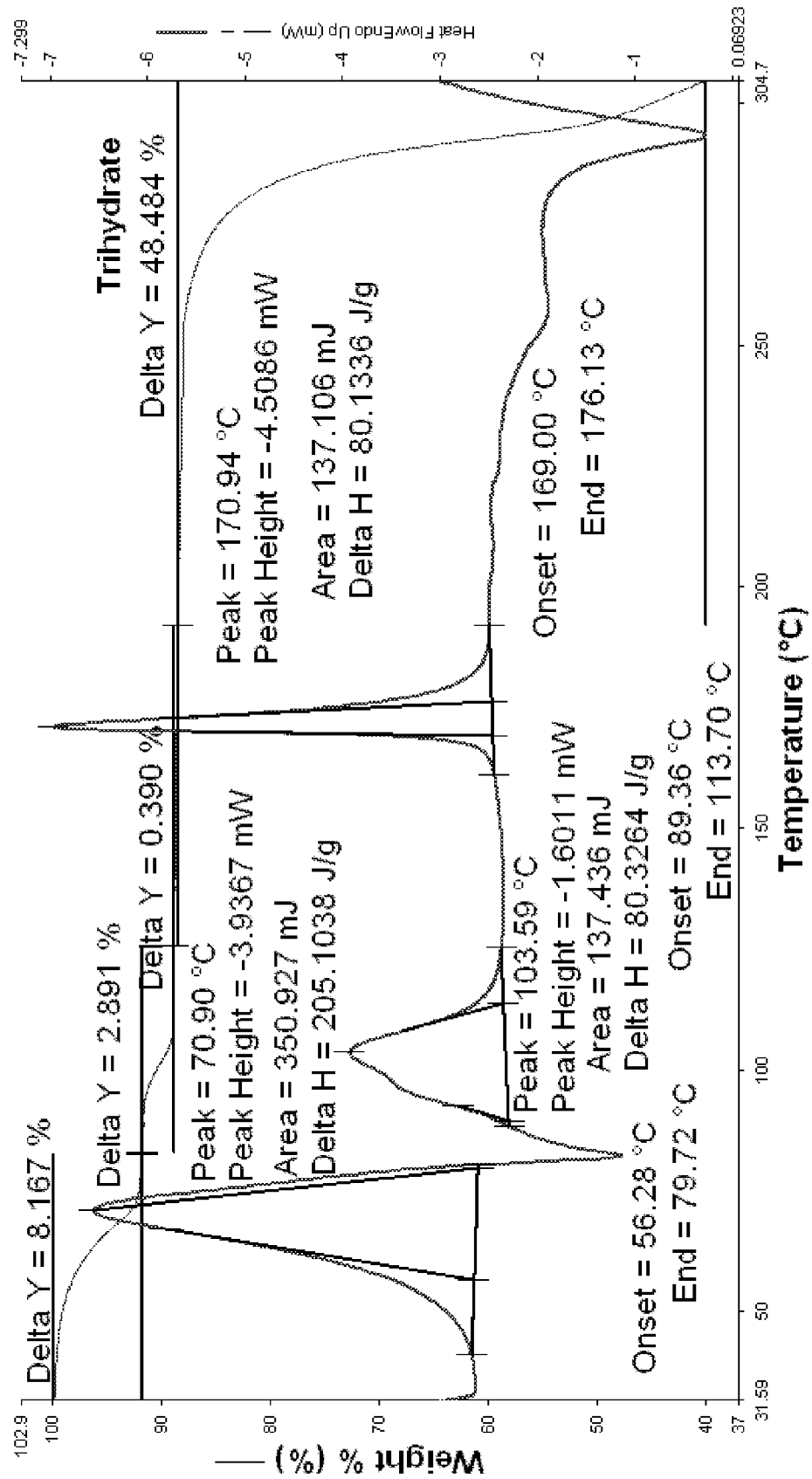
Figure 5:
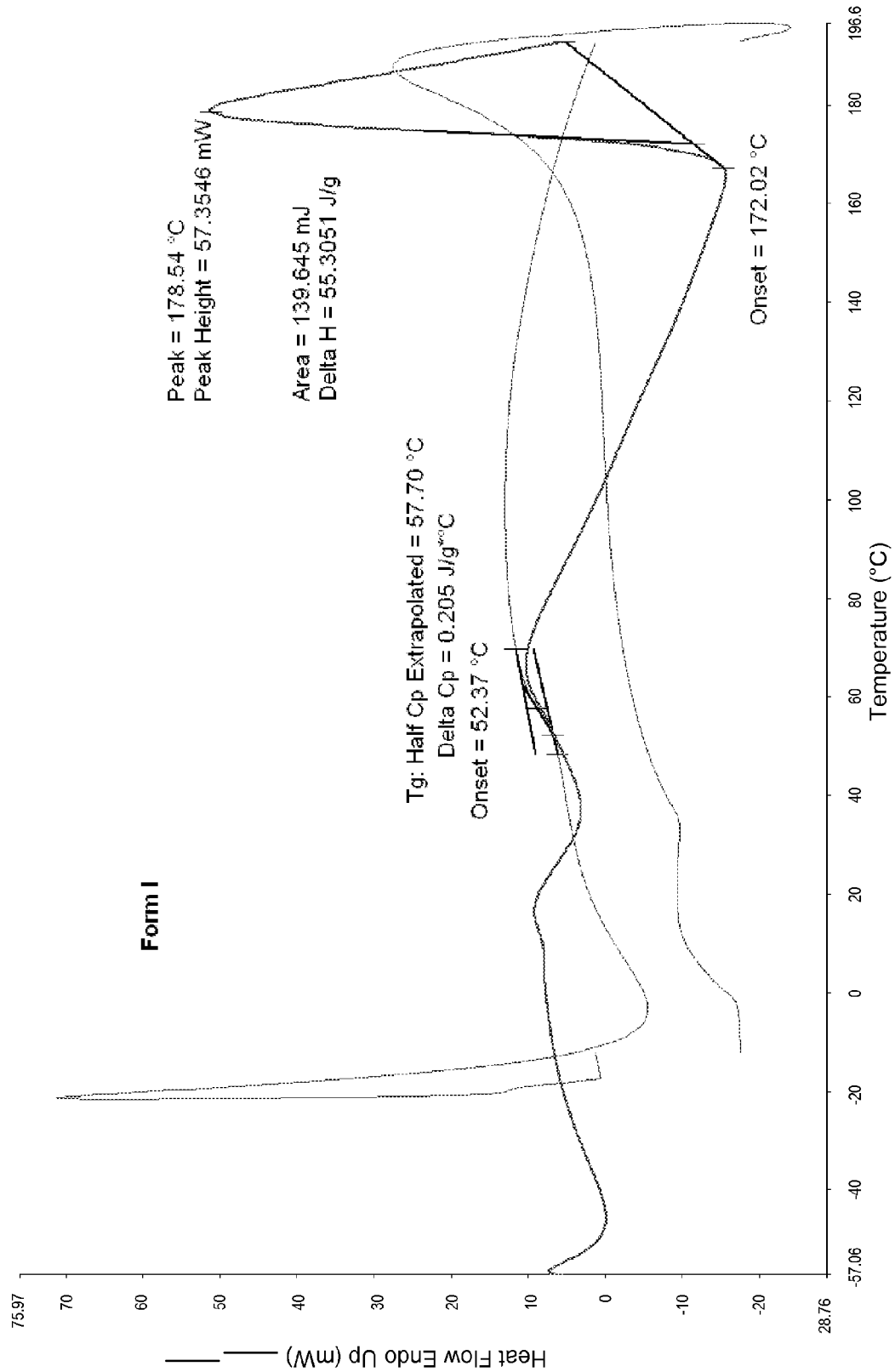
FIG. 5 is a HyperDSC Thermogram of Compound 1 Form I.
Figure 6:
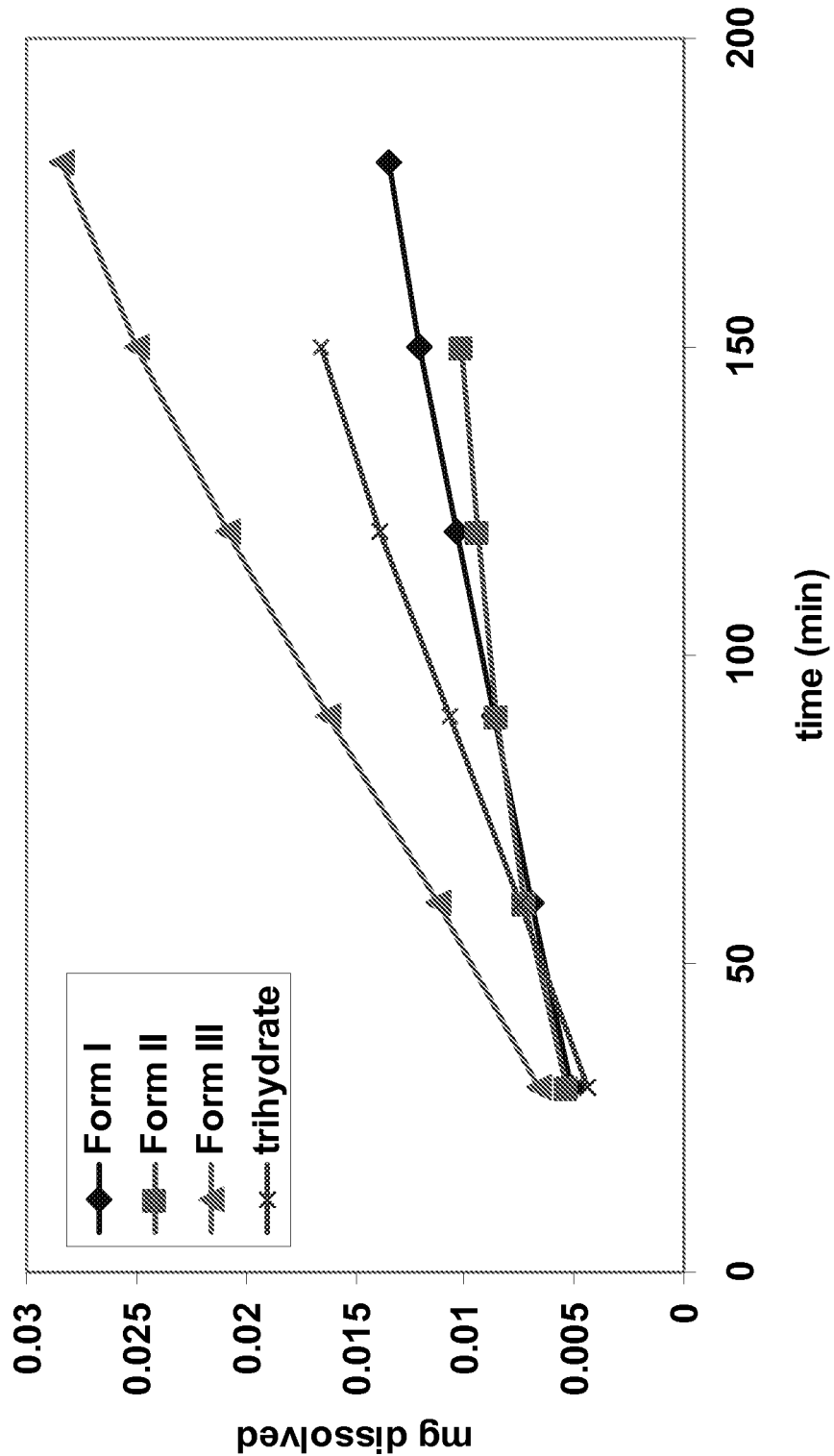
FIG. 6 depicts average dissolution profiles of the various physical forms of Compound 1.

Compound 1 (0.97 g) was weighed into a vial and THF: wafer (18% v/v) (8.95 mL) added. This mixture was shaken to give a cloudy solution and a further 0.63 g Compound 1 added in portions with shaking until most of the total amount of solid added had precipitated from solution. The mixture was left to stand undisturbed at ambient temperature for 3 days, after which it was filtered under vacuum, dried and analyzed. Yield obtained was 1.08 g (60.2%). The solid generated was analyzed by XRPD, DSC and TGA (FIG. 4). HPLC analysis indicated 99.7% purity (area).

Example 2

Comparative Examples for the Preparation of Forms I, II, and III

Example 2.1

Manufacturing Example

Ethyl acetate (3.6 kg, 4L) was added to Compound 1 (1.192 kg) and heated to 60° C. to form a suspension. This was stirred at 60° C. for 30 minutes and cooled to <10° C., stirred at <10° C. for 137 minutes and isolated by filtration. The solid was dried under vacuum at 40-50° C. with a slight nitrogen bleed to yield 0.96 kg. XRPD confirmed the solid to be predominantly Form III with trace amount of Form I.

Other examples of typical isolations performed by someone skilled in the art can be found from the results of the polymorph screening experiments. Only considering the manufacturing solvent (ethyl acetate), typical methods of isolation do not result in Form I.

Example 2.2

Slurry at 20° C.: Ethyl acetate (1 mL) was Added to Compound 1 (Form II, 25 mg) and agitated in a sealed vial at 20° C. using an orbital shaker for 5 days. The sold was isolated by filtration and allowed to dry at ambient conditions prior to analysis XRPD confirmed the solid to be Form II.

Example 2.3

Antisolvent Crystallisation: Compound 1 (Form II, 26 mg) was suspended in ethyl acetate (0.9 mL) for 16 hours and filtered through a 0.2 µm PTFE filter. The saturated solution was added to magnetically stirred heptane (9 mL) at 20° C. Samples were left to stand for 4 days and any solids that formed were isolated and air-dried prior to analysis. XRPD confirmed the solid to be Form III.

Example 2.4

Evaporation: Ethyl acetate (1 mL) was added to Compound 1 (Form II, 26 mg) and agitated at 20° C. for 16 hours days prior to filtration through a 0.2 µm PTFE filter. The solution was allowed to evaporate at ambient conditions (7 days). XRPD confirmed the solid to be Form III.

Example 2.5

Cooling crystallisation is a method commonly employed by those skilled in the art for purification. Compound 1 is not appreciably soluble in ethyl acetate, and the example below would not be commercially viable. However, solvents which were identified as good solvents for cooling crystallisations include acetonitrile and toluene. Using variable input Form, solvent and concentration, the final crystal Form is not under control and mixtures are obtained.

Example 2.5.1

Cooling Crystallisation from Ethyl Acetate

Compound 1 (Form II, 94 mg) was suspended in ethyl acetate (0.9 mL) at 60° C. for 45 minutes prior to filtration through a heated 0.2 µm PTFE filter into a warm vial (40° C.). The filtered solution was cooled to −35° C. in a dry ice/acetonitrile bath and the precipitate isolated immediately by filtration and air-dried XRPD confirmed the solid to be a mixture of Form II and Form III.

Example 2.5.2

Cooling Crystallisation from Acetonitrile/toluene

Solvent (1 mL) was added to Compound 1 (Form II, 25 or 50 mg) and heated to 80° C. in a sealed vial. The solution was held at 80° C. for 30 minutes prior to cooling to 20° C. at 0.2° C./min. The solid was isolated by filtration and allowed to dry at ambient conditions prior to XRPD analysis. The results are shown in Table 3.

TABLE 3

Cooling crystallisations of Compound 1

| Input Batch | Solvent | Concentration (mg/mL) | XRPD pattern | Output Form |
|---|---|---|---|---|
| Compound 1 (Form II) | acetonitrile | 25 | A | II + III |
| | | 50 | B | I + II |
| | toluene | 25 | C | II |
| | | 50 | C | II |

Following the invention of Form I, it became evident that XRPD pattern B was in fact a mixture of Form I and Form II. Note that the assignment of the Forms in the output Form column in Table 3 was only possible following the isolation of each pure Form. Therefore, isolation of pure Form I was not trivial for a person skilled in the art.

Example 3

Characterisation of Forms I, II, III, and Trihydrate of Compound 1

Optical Microscopy

Figure 9:
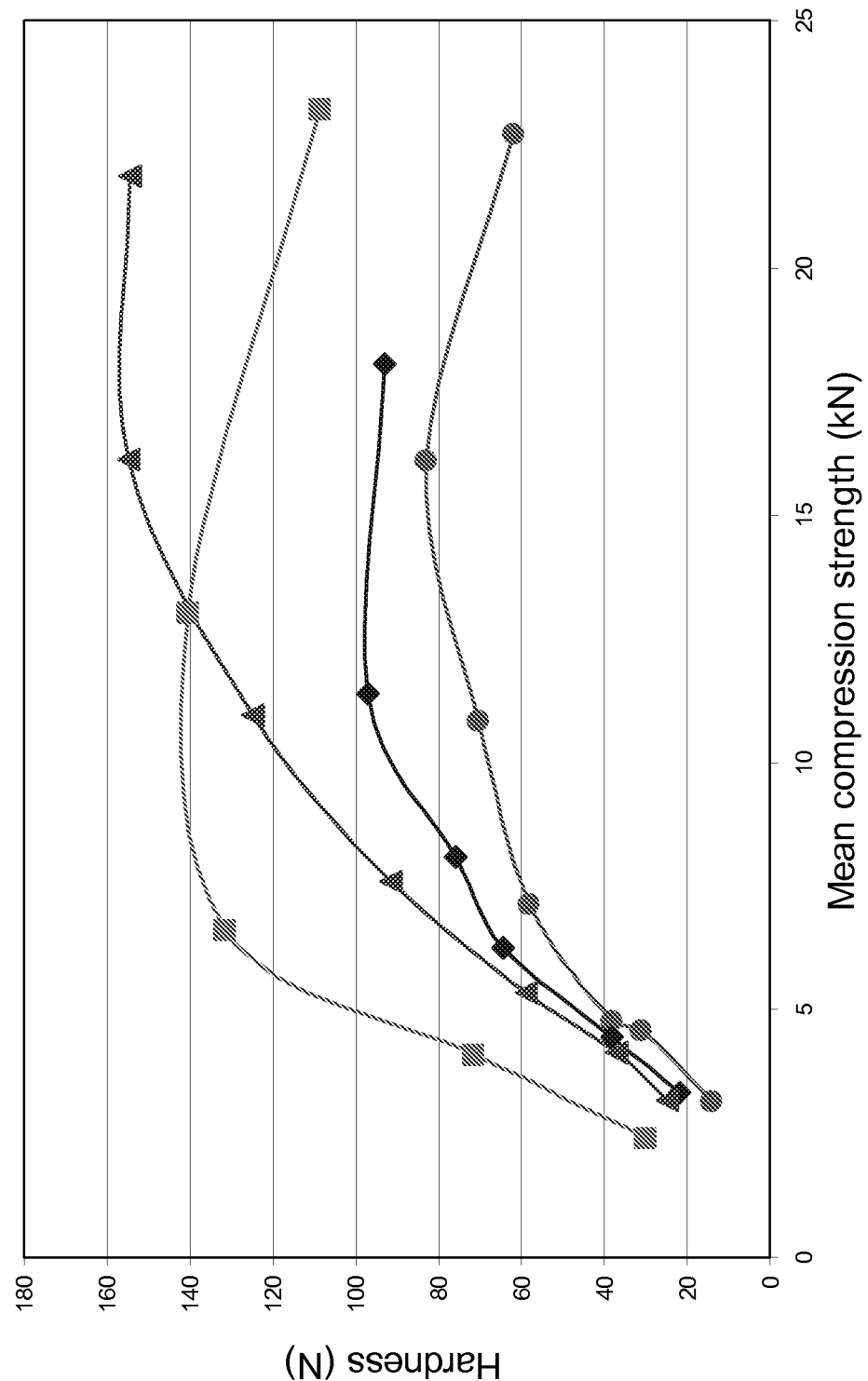
FIG. 9 is a graph depicting mean compression strength vs hardness of tablets obtained by various compression processes.

Optical microscopy was performed on Form I using (a) normal and (b) cross-polarized light (FIG. 9). Form I was shown to be highly crystalline under cross-polarized light. Typical particle size appeared to be in the range of 30-60 µm.

HyperDSC

HyperDSC was performed on this material (FIG. 10). The melt quenching of the Form I sample generated amorphous material in situ, which on re-heating allowed the glass transition temperature to be determined as 52.4° C.

Bulk Density

The bulk density of Compound 1 Form I was measured according to the method outlined above. The results are shown in Table 4. The bulk density of the Form I powder was found to at 0.52 g/mL (see Table 4).

TABLE 4

Bulk density measurements for Compound 1 Form I

| Experiment | Mass (g) | Volume (mL) | Density (g/mL) | Average (g/mL) | Appearance |
|---|---|---|---|---|---|
| 1 | 10.3813 | 19.75 | 0.526 | 0.519 | cream sold |
| 2 | 9.8478 | 19.00 | 0.518 | | |
| 3 | 9.6190 | 18.75 | 0.513 | | |

Specific Surface Area

The specific surface area results are shown in Table 5.

TABLE 5

Specific surface area results for Compound 1 Form I

| BET Surface Area ($m^2/g$) | Pore Volume ($cm^3/g$) BJH between 1.7-300 nm | | Pore Size (nm) 4V/A by BET | |
|---|---|---|---|---|
| | Adsorption | Desorption | Adsorption | Desorption |
| 0.2910 (±0.0056) | 0.000665 | 0.000742 | 9.44021 | 7.36920 |

DVS analysis

DVS analysis was used to investigate the hygroscopicity of Compound 1 Form I (FIG. 11). There was no initial mass loss observed on holding at 0 % RH, suggesting the sample contained little or no surface moisture. The overall weight gain up to 95% RH was 0.06% and weight gained up to 80% RH only 0.08%.

From those above findings, the sample was found to be non-hygroscopic according to the hygroscopicity classification in the European Pharmacopoeia (Table 6). After completion of the cycle, the sample was removed from the instrument and no weight change was observed.

TABLE 6

Hygroscopicity Classifications (Ph. Eur.)

| CLASSIFICATION | WEIGHT INCREASE AT 80% RH (25° C.) |
|---|---|
| Non hygroscopic | <0.2% |
| Sightly hygroscopic | ≥0.2% and <2% |
| Hygroscopic | ≥2% and <15% |
| Very hygroscopic | ≥15% |
| Deliquescent | sufficient water is absorbed to form a liquid |

Solubility

The solubility of Compound 1 Form I was determined by two different methods. The EP (European Pharmacopoeia) method is an aliquot addition method which gives a rough assessment of kinetic solubility. The equilibrium method requires the suspension of solid for an extended period in the dissolving medium. Although more accurate, the latter method has a tendency to generate a more stable physical form in situ, leading to lower solubility than the true solubility of the sample. The EP method indicated solubility of Compound 1 Form I to be insoluble in water and be soluble in ethanol at 33-100 mg/ml.

The concentration of the samples was assessed by HPLC. Results are shown in Table 7.

TABLE 7

Mean solubility values for Compound 1 Form I at pH 5.1 and 7.0

| | MEAN SOLUBILITY (MG/G) | |
|---|---|---|
| DAY | pH 5.1 | pH 7.0 |
| 1 | 1.101 | 0.074 |
| 2 | 0.735 | 0.043 |
| 3 | 0.587 | 0.031 |
| 4 | 0.507 | 0.025 |

Example 4

Interconversion Experiments

The most robust method for determining the thermodynamically most stable Form at a given temperature involves suspension of all observed forms in a saturated solution, as the system will naturally gravitate to the lowest free energy Form. In solvent mediated conversions, seeds of all Forms are present and there is no activation energy barrier to interconversion. This technique is used to identify the 'true' transition temperature and the thermodynamic relationship between the Forms. In order to determine the order of stability between each individual form interconversion experiments were performed using suspensions of pairs of each form in ethyl acetate at 5, 10 and 15° C. and suspensions of all Forms together at 21° C. and 60° C. The stirred suspensions of Forms I, II and III were sampled after 0.5 hr (t0), after 1, 2 and 3 days (t1-3) and 6 and 10 days if required.

Interconversion at 5° C.

The dried samples were analyzed by XRPD and the mixture of forms I and II showed conversion to form II, form I and III converted to form I and form II and form III mixture converted towards form II. Therefore at 5° C., Form II was determined as being the thermodynamically most stable form and the order of stability was Form II>I>III.

Interconversion at 10° C.

The dried samples were analyzed by XRPD and the mixture of forms I and II showed conversion to form II, form I and III converted to form I and form II and form III mixture converted towards form II. Therefore at 10° C., Form II was determined as being the thermodynamically most stable form and the order of stability was Form II>I>III.

Interconversion at 15° C.

The dried samples were analyzed by XRPD and the mixture of forms I and II showed conversion to form II, form I and III converted to form I and form II and form III mixture converted towards form II. Therefore at 15° C., Form II was determined as being the thermodynamically most stable form and the order of stability was Form II>I>III.

Interconversion at 21° C.

The dried samples were analyzed by XRPD and the mixture of Forms I, II and III showed conversion to Form I. Therefore at 21° C., Form I was determined as being the thermodynamically most stable form.

Interconversion at 60° C.

The dried samples were analyzed by XRPD and the mixture of Forms I, II and III showed conversion to Form I. Therefore at 60° C., Form I was determined as being the thermodynamically most stable form.

Conclusions from the Interconversion Experiments

For the interconversion experiments conducted (at 5, 10, 15, 21 & 60° C.), the order of stability was Form II>I>III. This work suggests that Form II is the most stable polymorph at temperatures lower than 18±2° C., with Form I the most stable polymorph at all higher temperatures (up to the melting point).

Form III has an enantiotropic relationship with Form I and Form II. The transition temperature for Form I to III occurs between 2 and 5° C., as evidenced from the interconversion experiments and observations of suspensions held in the refrigerator. As the melting point of Form II is higher than Form III, and Form II is more stable at 5-15° C., it follows that if a transition temperature exists between Form II and Form III, it will be <5° C. Indeed, form II and III may be monotropically related, meaning that Form II would be more stable than Form III at all temperatures.

It should be emphasized that these interconversions were mediated by suspension in solvent with the presence of seeds of each Form. In the solid state, and especially as a pure Form, conversion to another polymorph may not occur even after years in storage.

Example 5

Critical Water Activity

Experiments to determine the critical water activity level with respect to trihydrate formation were performed in acetone/water. Different % v/v ratios of water in acetone were used for suspensions at 21° C. The results indicate that the critical winter activity in acetone lies between 2 and 3% v/v water. Using the Wilson VLE model, this equates to 0.38-0.49 or 0.35-0.44 using the UNIFAC model. This provides useful information for process chemists and formulators in later development.

Example 6

Intrinsic Dissolution Rate (IDR)

Three samples of Form I, II, III and trihydrate were checked for IDR in USP pH 5.0 buffer. The samples were checked for any changes in their surface after dropping into the dissolution medium. Capping of the surface was observed in two of the three pellets of Form I. Capping is typically observed in samples having large particle size where air gets entrapped between the larger particles when compressed into a pellet. The particles relax on contact with water during dissolution, causing capping of the surface. So IDR was calculated for Form I based on drug release from one non capped pellet. No changes in surface were observed for the rest of the polymorph samples. The samples were collected manually through a cannula fitted with 10 μm inline filters. The samples collected from dissolution run were analyzed by HPLC.

The average of all three runs was used to plot and calculate the IDR of samples, with the exception of Form I. The average dissolution profile for each Form is shown in FIG. 12. The intrinsic dissolution rate for the various forms in pH 5.0 media is shown in Table 8 Within the error of the current test, the Form I and II are indistinguishable in dissolution rate.

TABLE 8

Intrinsic dissolution rate of Compound 1 forms at pH 5.0

| FORM | IDR (mg cm$^{-2}$ min$^{-1}$) | RSD (3 runs) |
|---|---|---|
| Form I | 0.101 | 2.5% |
| Form II | 0.098 | 45.9% |
| Form III | 0.266 | 4.6% |
| Trihydrate | 0.184 | 13.0% |

The trihydrate form had a higher IDR than two of the anhydrous forms (I and II). As hydrates are the most stable form in aqueous solvent by definition, hydrates are therefore less soluble than anhydrous forms. In theory, intrinsic dissolution rate is assumed to be proportional to the equilibrium solubility (i.e. the Noyes-Whitney relationship). Since the earliest dissolution studies on pharmaceutical compounds, it has been noted that the dissolution rate of anhydrous phases exceeds that of the corresponding hydrate phase in aqueous media as hydrates possess a lower activity and are therefore more stable (less soluble) than anhydrous forms. It is well documented that the vast majority of pharmaceutical substances obey this general rule, for example, theophylline, ampicillin, ciplofloxacin and oxyphenbutazone. It should be noted that there have been hundreds of other examples reported. Only in an unusually small number of cases have hydrate phases been found to dissolve faster than anhydrous phases, e.g. erythromycin and alprazolam. In this context, the significantly higher dissolution rate of the Compound 1 trihydrate over Form I and II was unexpected and surprising.

However, other factors are known to affect IDR results and hydrates with higher IDR than anhydrous forms have been reported in the literature (Pharm Dev. & Tech., 1(4), 373-380, 1998). No adequate explanation for this phenomenon has been addressed on the wider literature. Micro-environmental differences related to the diffusion film are one possibility.

After the dissolution test, the remaining portion of the pressed discs were dried in air and examined by XRPD. No change in Form was observed for any of the test discs.

Example 7

Reprocessing of Compound 1 Lots to Form I

Compound 1 (~440 g), Form II by XRPD analysis, was converted into Form I by seeding of a slurry at elevated temperature in ethyl acetate. The amount recovered was 412.35 g (93.3%) and HPLC analysis indicated 99.8% purity (area). The solid generated was analyzed by XRPD, DSC and TGA (—FIG. 13). XRPD analysis corresponded to Form I, DSC indicated the onset of melting was at 169.2° C. and TGA indicated a weight loss of 0.29% up to complete melting, which confirms that the amount of volatiles remaining in the sample was not significant.

1H and 13C NMR 1H and 13C NMR was also used to characterize Compound 1 structure. Based on the atom labelling shown in FIG. 14, the spectral analysis corresponded to the known chemical structure (assignment in Table 9). Carbon assignments from HSQC (protonated carbons) and HMBC (quaternary carbons based on 3-bond couplings) were calibrated against peaks observed in the one dimensional $^{13}$C spectrum. Overlap of H5 and H14 complicates assignment of C4 and C11.

TABLE 9

NMR Spectral Data for Compound 1

| CARBON NUMBER | δ 1H/ppm | δ 13C/ppm |
|---|---|---|
| 1, 2 | 2.70 (singlet, 6H) | 45.25 |
| 3 | N/A | 146.49 |
| 4 | N/A | 127.67 |
| 5 | 6.76 (singlet, 1H) | 102.34 |
| 6 | 6.40 (singlet, 1H) | 108.59 |
| 7, 8 | N/A | 147.80, 144.93 |
| 9 | 5.89 (singlet, 2H) | 101.61 |
| 10 | N/A | 146.32 |
| 11 | N/A | 127.41 |
| 12 | N/A | 141.26 |
| 13 | NA | 151.09 |
| 14 | 6.75 (doublet J = 6.0 Hz, 1H) | 97.71 |
| 15 | 7.84 (doublet J = 6.0 Hz, 1H) | 140.53 |
| 16 | 4.24 (triplet J = 6.6 Hz, 2H) | 45.50 |
| 17 | 2.91 (triplet J = 6.6 Hz, 2H) | 50.02 |
| 18 | 2.29 (singlet, 2H) | 62.23 |
| 19 | N/A | 31.61 |
| 20, 21, 22 | 0.82 (singlet, 9H) | 27.6 |

Particle Size Distribution

Particle size distribution of Compound 1 was determined using the Sympatec HELOS Laser Diffractometer. The particle size distribution profile (FIG. 15 and Table 9) indicated a unimodal distribution with 90% of the particles smaller than 84.93 µm. Optical microscopy was also performed on the Form I solid under cross-polarized light (FIG. 16). Microscopy confirmed that the particles were highly crystalline and that most particles were <85 µm, with a typical particle size distribution of around 40-70 µm.

TABLE 10

Summary of laser diffraction measurements on Compound 1 Form I

| D10 (µm) | D50 (µm) | D90 (µm) | Modality |
|---|---|---|---|
| 5.95 | 36.02 | 84.93 | unimodal |

Modifications and variations of the invention will be obvious to those skilled in the art from the foregoing detailed description of the invention. Such modifications and variations are intended to come within the scope of the appended claims.

While this invention has been particularly shown and described with references to preferred embodiments thereof, it will be understood by those skilled in the art that various changes in form and details may be made therein without departing from the scope of the invention encompassed by the appended claims.

Example 8

Compression Capacities—Tablet Manufacturing

Two different compression processes were used to obtain tablets.
- direct compression: the powder blend is directly compressed
- wet granulation: the powder blend is first granulate with water and dried, and then the granules were compressed.

Comparisons were performed on
Compound 1 under crystalline forms tablets produced by
  direct compression (represented by lozenge in FIG. 9)
  wet granulation (represented by a circle in FIG. 9)
Compound 1 as the trihydrate tablet produced by
  direct compression (represented by a triangle in FIG. 9)
  wet granulation process (represented by a square in FIG. 9)

All tablets have the same composition:

| Products | Theoretical quantity (%) |
|---|---|
| Compound 1 | 40 |
| Mannitol | 33 |
| Microcrystalline Cellulose | 20 |
| Crospovidone | 5 |
| Aerosil | 0.5 |
| Magnesium stearate | 1.5 |
| Blend | 100 |

Process:

The material used for the process was standard pharmaceutical material Powder blend was performed with pharmaceutical rotative blender (size must be adapted on volume of powder mix). Wet granulation was performed with pharmaceutical granulator (size must be adapted on volume of powder mix) Direct compression was performed with industrial rotative press, and for development batch with simulator of rotative press.

Results

XRPD analysis performed on active pharmaceutical ingredient (API) and subsequent tablets showed that both the crystalline form and trihydrate form remain unchanged, demonstrating that the tableting process has not changed the API form. All tablets are immediate release oral form according to European Pharmacopeia specifications. The mean compression strength—hardness graph obtained on Stylcam (FIG. 9) demonstrates better hardness for tablets containing trihydrate at the same compression forces that correspond to a better compressibility capacity. Powder blend containing trihydratre form present better flowability and tablets containing trihydratre form present better cohesion Conclusion For direct compression, the trihydrate form was the most suitable for an industrial tabletting process. For wet granulation process, tablets could be obtained with the two kinds of API. However, tablets with trihydrate form present better compression properties.

It is particularly unexpected that another Form would have better compaction properties than another. There is no current methodology for prediction of compaction properties from crystal structure.

The invention claimed is:

1. A polymorphic form of Compound 1 characterized by an X-ray powder diffraction with a characteristic peak at 7.1° 2Theta:

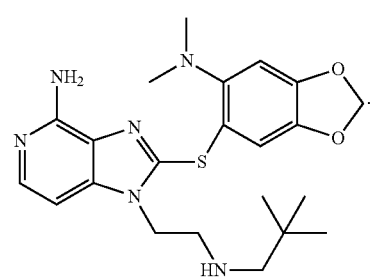

Compound 1

2. A polymorphic form of Compound 1 according to claim 1, characterized by an X-ray powder diffraction with characteristic peaks at about 7.1°, 9.6°, 9.8° 2Theta.

3. A polymorphic form of Compound 1 according to claim 1, characterized by an X-ray powder diffraction with characteristic peaks at about 7.1°, 9.6°, 9.8°, 12.2°, 18.3° 2Theta.

Figure 7:
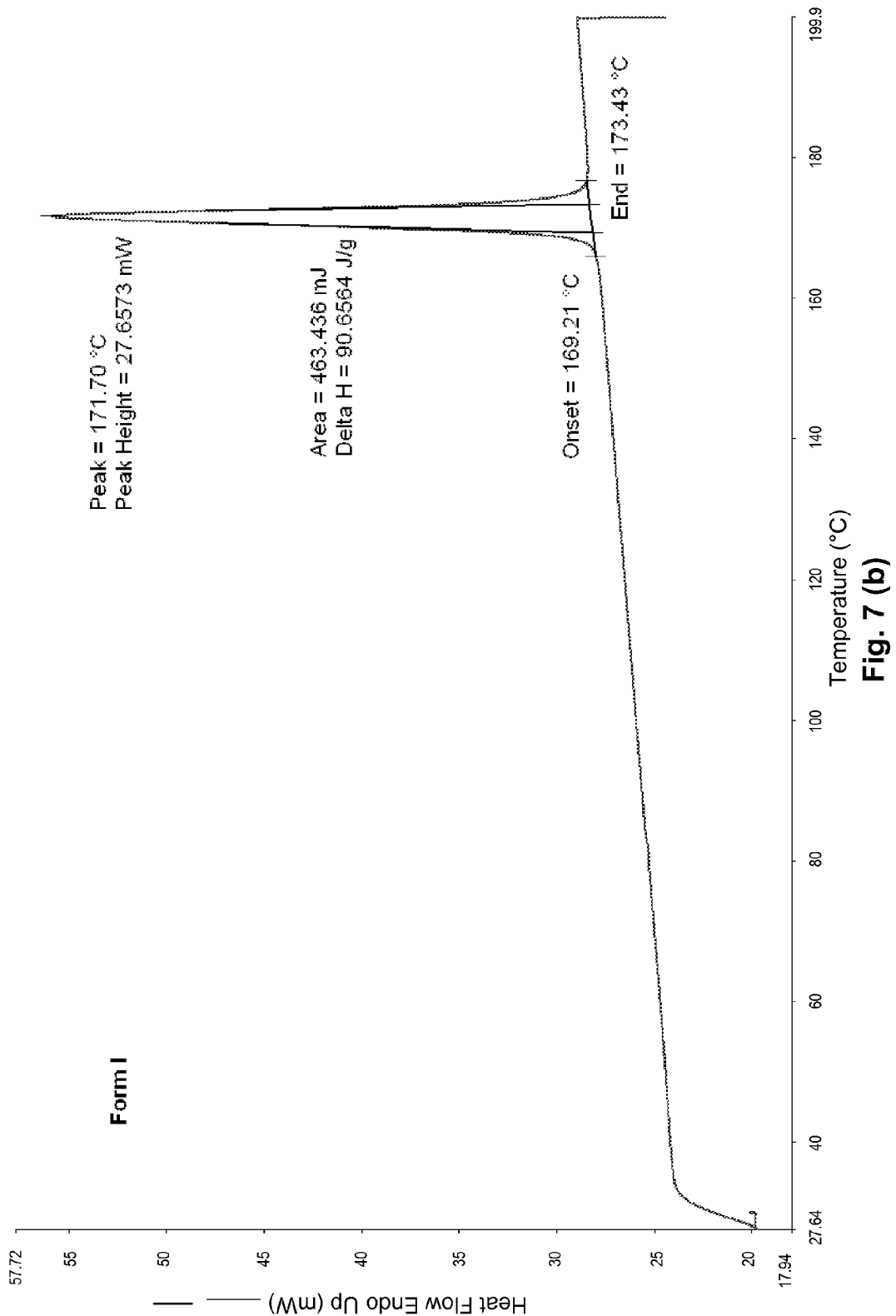
FIG. 7a-c is a graph depicting the (a) XRFD (b) DSC and (c) TG/DTA analysis of Compound 1 Form I.
Figure 7:
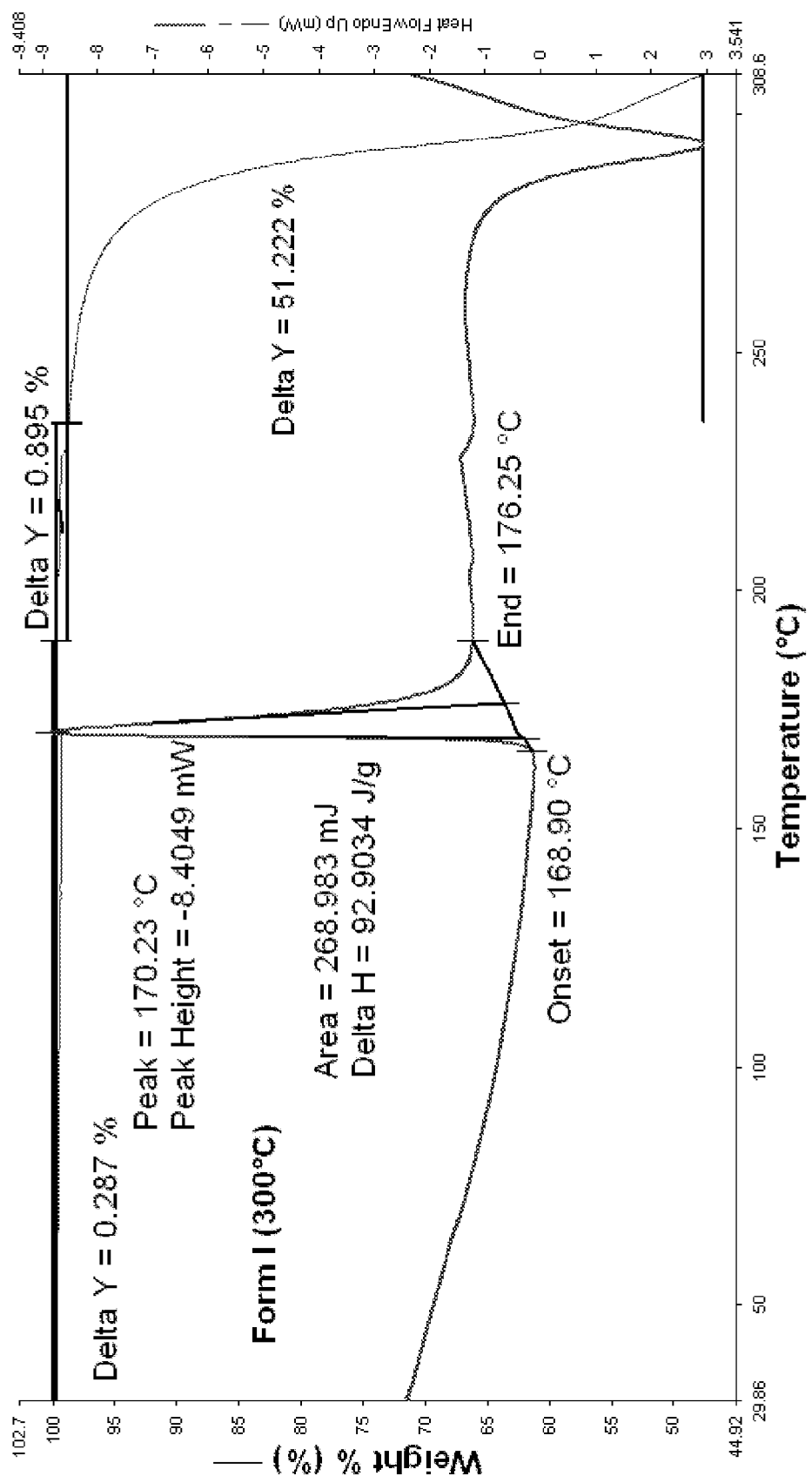
Figure 8:
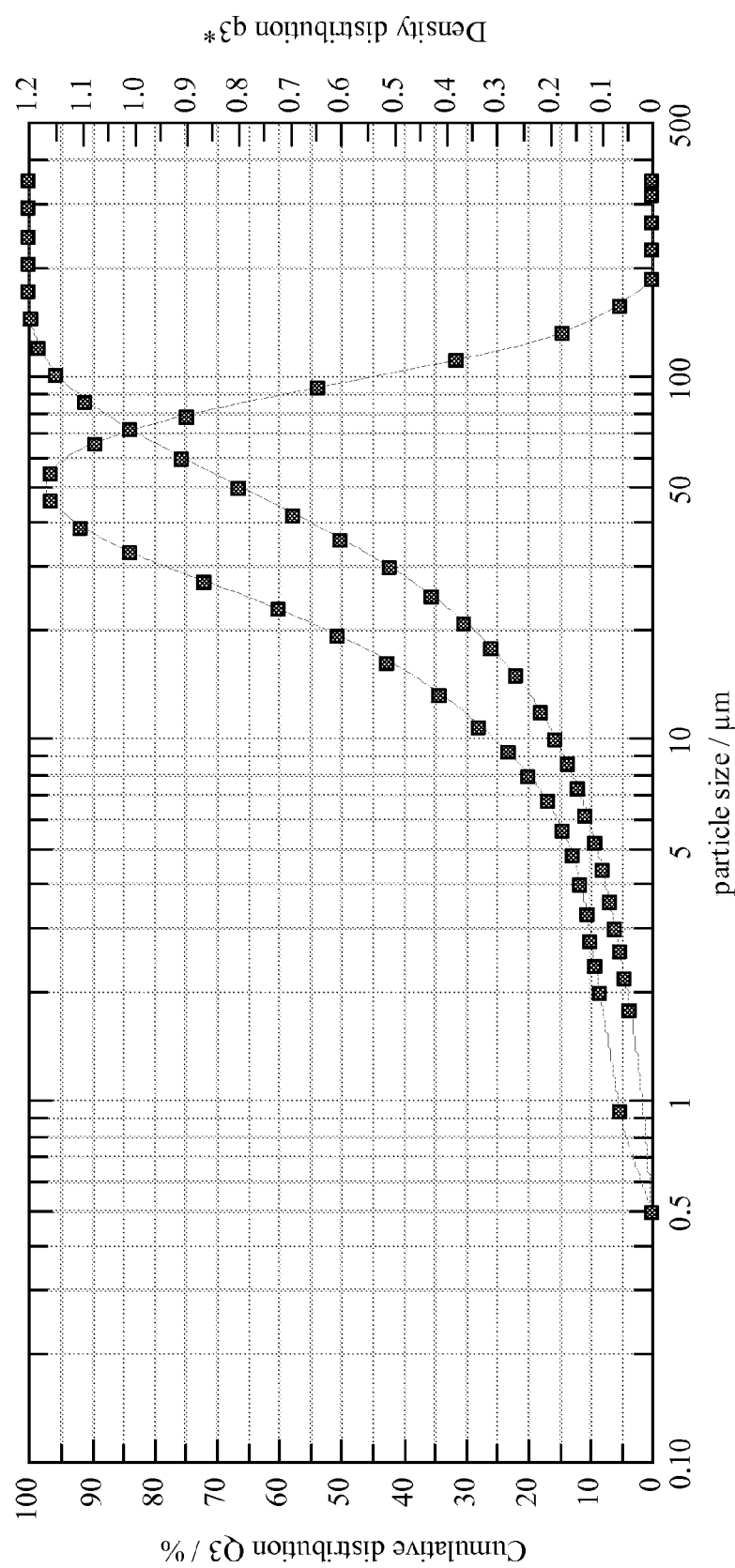
FIG. 8 is a graph of typical particle size distribution curves for Compound 1 Form I.

4. A polymorphic form according to claim 1 further characterized by the X-ray powder diffraction pattern of FIG. 7 (a).

5. A polymorphic form according to claim 1, further characterized by the DSC pattern of FIG. 7 (b).

6. A composition comprising a polymorphic form according to claim 1. wherein the compound is substantially free of the amorphous form of Compound 1.

7. A polymorphic form of Compound 1 characterized by an X-ray powder diffraction with a characteristic peak at about 8.0° 2Theta.

8. A polymorphic form according to claim 7 further characterized by the X-ray powder diffraction pattern of FIG. 2 (a).

9. A polymorphic form according to claim 7 further characterized by the DSC pattern of FIG. 2 (b).

10. A composition comprising a polymorphic form according to claim 7. wherein the compound is substantially free of the amorphous form of Compound 1.

11. A polymorphic form of Compound 1 characterized by an X-ray powder diffraction with a characteristic peak at about 8.1° 2Theta.

12. A polymorphic form of Compound 1 according to claim 11, characterized by an X-ray powder diffraction with characteristic peaks at about 5.9°, 8.1°, 12.8° 2Theta.

13. A polymorphic form of Compound 1 according to claim 11, characterized by an X-ray powder diffraction with characteristic peaks at about 5.9°, 8.1°, 8.8°, 11.0°, 12.8° 2Theta.

14. A polymorphic form according to claim 11 further characterized by the X-ray powder diffraction pattern of FIG. 3 (a).

15. A polymorphic form according to claim 11, further characterized by the DSC pattern of FIG. 3 (b).

16. A composition comprising a polymorphic form according to claim 11. wherein the compound is substantially free of the amorphous form of Compound 1.

17. A mixture of polymorphs comprising any of the polymorphs of claim 1.

18. A trihydrate solvate of Compound-1 characterized by the X-ray powder diffraction pattern of FIG. 4 (a).

19. A trihydrate solvate form according to claim 18 further characterized by the DSC pattern of FIG. 4 (b).

20. A composition comprising a trihydrate solvate form according claim 18 wherein the compound is substantially free of the amorphous form of Compound 1.

21. A pharmaceutical composition comprising the solvate according to claim 18.

22. The pharmaceutical composition according to claim 21 as a tablet.

* * * * *